US008685663B2

(12) United States Patent
Murakami et al.

(10) Patent No.: US 8,685,663 B2
(45) Date of Patent: Apr. 1, 2014

(54) METHOD, REAGENT AND KIT FOR MEASURING CHOLESTEROL IN LOW-DENSITY LIPOPROTEINS

(75) Inventors: Tomomi Murakami, Shizuoka (JP); Tomoko Aratake, Shizuoka (JP); Shingo Mishima, Shizuoka (JP); Hideyuki Kuwata, Shizuoka (JP)

(73) Assignee: Kyowa Medex Co., Ltd., Tokyo (JP)

( * ) Notice: Subject to any disclaimer, the term of this patent is extended or adjusted under 35 U.S.C. 154(b) by 127 days.

(21) Appl. No.: 13/128,444

(22) PCT Filed: Nov. 13, 2009

(86) PCT No.: PCT/JP2009/069371
§ 371 (c)(1),
(2), (4) Date: May 20, 2011

(87) PCT Pub. No.: WO2010/055916
PCT Pub. Date: May 20, 2010

(65) Prior Publication Data
US 2011/0223626 A1 Sep. 15, 2011

(30) Foreign Application Priority Data
Nov. 14, 2008 (JP) .................................. 2008-291608

(51) Int. Cl.
*C12Q 1/60* (2006.01)
*C12N 9/16* (2006.01)
*C12N 9/04* (2006.01)

(52) U.S. Cl.
USPC .............................. 435/11; 435/190; 435/196

(58) Field of Classification Search
USPC ............................................ 435/11, 190, 196
See application file for complete search history.

(56) References Cited

U.S. PATENT DOCUMENTS

| 5,814,472 | A | 9/1998 | Miki et al. |
| 5,885,788 | A | 3/1999 | Miki et al. |
| 6,194,164 | B1 | 2/2001 | Matsui et al. |
| 6,794,157 | B1 | 9/2004 | Sugiuchi |
| 2005/0170447 | A1 | 8/2005 | Lawrence et al. |

FOREIGN PATENT DOCUMENTS

| CA | 2 260 689 | 8/2000 |
| CN | 1253627 A | 5/2000 |
| CN | 1318107 | 10/2001 |
| CN | 1742098 A | 3/2006 |
| EP | 0 990 904 | 4/2000 |
| EP | 1 555 326 | 7/2005 |
| EP | 1 580 279 | 9/2005 |
| EP | 1 953 240 | 8/2008 |
| JP | 09-313200 | 9/1997 |
| JP | 10-038888 | 2/1998 |
| JP | 10-84997 | 4/1998 |
| JP | 10-306188 | 11/1998 |
| JP | 11-030617 | 2/1999 |
| JP | 2002-202314 | 7/2002 |
| JP | 2002-343979 | 11/2002 |
| JP | 2007-523325 | 8/2007 |
| WO | 98/47005 | 10/1998 |
| WO | 00/17388 | 3/2000 |
| WO | 03/023397 | 3/2003 |
| WO | 2004/048605 | 6/2004 |
| WO | 2005/074609 | 8/2005 |
| WO | 2007/072013 | 6/2007 |

OTHER PUBLICATIONS

Friedewald, et al., "Estimation of the Concentration of Low-Density Lipoprotein Cholesterol in Plasma, Without Use of the Preparative Ultracentrifuge", Clinical Chemistry, vol. 18, No. 6 (1972) 499-502.
Hatch, et al., "Practical Methods for Plasma Lipoprotein Analysis", Advan. Lipid Res., vol. 6 (1968) 1-69.
Sugiuchi, et al., "Homogeneous assay for measuring low-density lipoprotein cholesterol in serum with triblock copolymer and alpha-cyclodextrin sulfate", Clinical Chemistry, vol. 44, No. 3 (1998) 522-31.

*Primary Examiner* — Susan Hanley
(74) *Attorney, Agent, or Firm* — Fitzpatrick, Cella, Harper & Scinto

(57) ABSTRACT

A method for measuring cholesterol in low-density lipoprotein contained in a sample, which comprises reacting a sample with (i) a combination of cholesterol ester hydrolase and cholesterol oxidase or (ii) a combination of cholesterol ester hydrolase, an oxidized coenzyme and cholesterol dehydrogenase in the presence of: [a] a polyoxyethylene-polyoxyalkylene alkylaryl ether; [b] one or more surfactants selected from the group consisting of a polyoxyethylene-polyoxyalkylene copolymer, a polyoxyethylene alkenyl ether, a polyoxyethylene branched alkyl ether, and a polyoxyethylene-polyoxyalkylene branched alkyl ether; [c] one or more surfactants selected from the group consisting of a primary amine, a secondary amine, a tertiary amine, and a quaternary ammonium; and [d] a polyanion, and measuring a substance formed or consumed in the reaction.

33 Claims, No Drawings

METHOD, REAGENT AND KIT FOR MEASURING CHOLESTEROL IN LOW-DENSITY LIPOPROTEINS

TECHNICAL FIELD

The present invention relates to a method and a kit for measuring cholesterol (hereinafter abbreviated as LDL-C) in low-density lipoprotein (hereinafter referred to as LDL) contained in a sample.

BACKGROUND ART

LDL plays a role of supplying cholesterol to peripheral cells, and it is a direct factor for various types of arteriosclerosis including coronary arteriosclerotic disease as a typical example. An increase in LDL-C is a principal risk factor for arteriosclerotic diseases. Thus, fractional determination of such LDL-C is clinically useful.

Conventional methods for quantitatively determining LDL-C include an ultracentrifugation method, an electrophoresis, and a calculation method using a Friedewald formula.

The ultracentrifugation method is a method involving utilization of a difference in the gravities of lipoproteins, which comprises separating LDL with the use of an ultracentrifuge and then measuring the cholesterol amount (Non Patent Literature 1).

However, separation operations according to such an ultracentrifugation method are complicated, and thus, this method is disadvantageous in terms of promptness and simplicity.

The electrophoresis includes a method utilizing a difference in the charges of lipoproteins, which comprises separating LDL using an agarose gel as a supporting medium, and a method utilizing a difference in the particle sizes of lipoproteins, which comprises separating LDL using a polyacrylamide gel as a supporting medium. However, the electrophoresis is poor in terms of quantitative capability, and it is problematic in terms of simplicity, economic efficiency, etc.

In the calculation method using a Friedewald formula, based on the measurement values of total cholesterol (hereinafter abbreviated as T-C), cholesterol (hereinafter abbreviated as HDL-C) in high-density lipoprotein (hereinafter referred to as HDL), and total triglyceride (hereinafter abbreviated as T-TG), the amount of LDL-C is calculated according to the formula shown below (Non Patent Literature 2).

(LDL-C)=(T-C)−(HDL-C)−(T-TG)/5

However, since this method is affected by the content of T-TG in the serum or diet, it has a problem in accuracy.

In recent years, there have been reported methods for quantitatively determining LDL-C, which can be applied to commonly used auto-analyzers, without requiring separation operations performed by the ultracentrifugation method and the like.

Among such methods, the following methods for quantitatively determining LDL-C are known.

A method for quantitatively determining LDL-C contained in a test sample, which comprises: a first step of allowing cholesterol esterase and cholesterol oxidase to act on a test sample in the presence of a surfactant acting on lipoproteins other than LDL, and then removing the formed hydrogen peroxide, to quench cholesterol in HDL, very low-density lipoprotein (hereinafter referred to as VLDL) and a chylomicron contained in the test sample; and a second step of quantitatively determining residual cholesterol contained in the sample (Patent Literature 1).

A method for quantitatively determining LDL-C, which comprises: adding a surfactant selected from a polyoxyethylene alkylene phenyl ether and a polyoxyethylene alkylene tribenzyl phenyl ether and an enzyme reagent for measuring cholesterol to the serum; reacting these reagents preferentially with cholesterols in HDL and VLDL among lipoproteins; and measuring the reaction amount of residual cholesterol (Patent Literature 2).

A method, which comprises adding a polyoxyethylene derivative, a polyoxyethylene-polyoxypropylene copolymer and enzymes for measuring cholesterol to a biological sample, and selectively measuring LDL-C among lipoproteins (Patent Literature 3).

A method for measuring LDL-C, which comprises measuring LDL-C contained in a biological sample in the presence of dimethyl-α-cyclodextrin and/or poly-β-cyclodextrin (Patent Literature 4).

A method for directly and selectively measuring cholesterol contained in a sample comprising at least one of chylomicron, HDL, LDL and VLDL, wherein LDL-C contained in the sample is quantitatively determined in the presence of a compound containing a phospholipid or a phospholipid-like group (Patent Literature 5).

However, it has been desired to develop a method and a kit for more simply and precisely measuring LDL-C contained in a sample.

CITATION LIST

Patent Literature

[Patent Literature 1] Japanese Patent Laid-Open No. 10-38888
[Patent Literature 2] Japanese Patent Laid-Open No. 9-313200
[Patent Literature 3] International Publication No. WO00/17388
[Patent Literature 4] Japanese Patent Laid-Open No. 11-30617
[Patent Literature 5] Japanese Patent Laid-Open No. 2002-202314

Non Patent Literature

[Non Patent Literature 1] Advanced Lipid Research (Adv. Lipid Res.), Vol. 6, p. 1, 1968
[Non Patent Literature 2] Clinical Chemistry (Clin. Chem.), Vol. 18, p. 499, 1972

SUMMARY OF INVENTION

Problems to be Solved by the Invention

It is an object of the present invention to provide a method, a reagent, and a kit for simply and precisely measuring LDL-C contained in a sample.

Means for Solving the Problems

As a result of intensive studies regarding a method for measuring LDL-C, the present inventors have found that LDL-C contained in a sample can be simply and precisely measured, without removing cholesterols in lipoproteins other than LDL and without performing physical fractionation operations on such lipoproteins, by reacting the sample with a combination of cholesterol ester hydrolase and cholesterol oxidase, or with a combination of cholesterol ester hydrolase, an oxidized coenzyme and cholesterol dehydrogenase in the presence of specific surfactants and a polyanion, thereby completed the present invention. Specifically, the present invention relates to the following (1) to (31):

(1) A method for measuring cholesterol in low-density lipoprotein contained in a sample, which comprises
reacting the sample with (i) a combination of cholesterol ester hydrolase and cholesterol oxidase or (ii) a combination of cholesterol ester hydrolase, an oxidized coenzyme and cholesterol dehydrogenase in the presence of:
[a] a polyoxyethylene-polyoxyalkylene alkylaryl ether;
[b] one or more surfactants selected from the group consisting of a polyoxyethylene-polyoxyalkylene copolymer, a polyoxyethylene alkenyl ether, a polyoxyethylene branched alkyl ether, and a polyoxyethylene-polyoxyalkylene branched alkyl ether;
[c] one or more surfactants selected from the group consisting of a primary amine, a secondary amine, a tertiary amine, and a quaternary ammonium; and
[d] a polyanion, and
measuring a substance formed or consumed in the reaction.

(2) A method for measuring cholesterol in low-density lipoprotein contained in a sample, which comprises
reacting the sample with (i) a combination of cholesterol ester hydrolase and cholesterol oxidase or (ii) a combination of cholesterol ester hydrolase, an oxidized coenzyme and cholesterol dehydrogenase in the presence of:
[a] a polyoxyethylene-polyoxyalkylene alkylaryl ether;
[b1] a polyoxyethylene-polyoxyalkylene copolymer;
[c] one or more surfactants selected from the group consisting of a primary amine, a secondary amine, a tertiary amine, and a quaternary ammonium; and
[d] a polyanion, and
measuring a substance formed or consumed in the reaction.

(3) A method for measuring cholesterol in low-density lipoprotein contained in a sample, which comprises
reacting the sample with (i) a combination of cholesterol ester hydrolase and cholesterol oxidase or (ii) a combination of cholesterol ester hydrolase, an oxidized coenzyme and cholesterol dehydrogenase in the presence of:
[a] a polyoxyethylene-polyoxyalkylene alkylaryl ether;
[b1] a polyoxyethylene-polyoxyalkylene copolymer;
[b2] one or more surfactants selected from the group consisting of a polyoxyethylene alkenyl ether, a polyoxyethylene branched alkyl ether, and a polyoxyethylene-polyoxyalkylene branched alkyl ether;
[c] one or more surfactants selected from the group consisting of a primary amine, a secondary amine, a tertiary amine, and a quaternary ammonium; and
[d] a polyanion, and
measuring a substance formed or consumed in the reaction.

(4) The method according to any one of (1) to (3) above, wherein the quaternary ammonium salt is a trimethylalkylammonium salt or a benzyldimethylalkylammonium salt.

(5) The method according to any one of (1) to (3) above, wherein the tertiary amine is a dimethylalkylamine.

(6) The method according to any one of (1) to (5) above, wherein the formed substance is hydrogen peroxide.

(7) The method according to (6) above, wherein the hydrogen peroxide is measured using a reagent for measuring hydrogen peroxide.

(8) The method according to any one of (1) to (5) above, wherein the formed substance is a reduced coenzyme.

(9) The method according to (8) above, wherein the reduced coenzyme is measured using a reagent for measuring a reduced coenzyme.

(10) A reagent for measuring cholesterol in low-density lipoprotein contained in a sample, which comprises:
[a] a polyoxyethylene-polyoxyalkylene alkylaryl ether;
[b] one or more surfactants selected from the group consisting of a polyoxyethylene-polyoxyalkylene copolymer, a polyoxyethylene alkenyl ether, a polyoxyethylene branched alkyl ether, and a polyoxyethylene-polyoxyalkylene branched alkyl ether;
[c] one or more surfactants selected from the group consisting of a primary amine, a secondary amine, a tertiary amine, and a quaternary ammonium;
[d] a polyanion; and cholesterol ester hydrolase and cholesterol oxidase.

(11) A reagent for measuring cholesterol in low-density lipoprotein contained in a sample, which comprises:
[a] a polyoxyethylene-polyoxyalkylene alkylaryl ether;
[b1] a polyoxyethylene-polyoxyalkylene copolymer;
[c] one or more surfactants selected from the group consisting of a primary amine, a secondary amine, a tertiary amine, and a quaternary ammonium;
[d] a polyanion; and cholesterol ester hydrolase and cholesterol oxidase.

(12) A reagent for measuring cholesterol in low-density lipoprotein contained in a sample, which comprises:
[a] a polyoxyethylene-polyoxyalkylene alkylaryl ether;
[b1] a polyoxyethylene-polyoxyalkylene copolymer;
[b2] one or more surfactants selected from the group consisting of a polyoxyethylene alkenyl ether, a polyoxyethylene branched alkyl ether, and a polyoxyethylene-polyoxyalkylene branched alkyl ether;
[c] one or more surfactants selected from the group consisting of a primary amine, a secondary amine, a tertiary amine, and a quaternary ammonium;
[d] a polyanion; and cholesterol ester hydrolase and cholesterol oxidase.

(13) The reagent according to any one of (10) to (12) above, which further comprises a reagent for measuring a substance formed as a result of the reaction of the cholesterol ester hydrolase and the cholesterol oxidase with the sample.

(14) The reagent according to (13) above, wherein the substance formed as a result of the reaction of the cholesterol ester hydrolase and the cholesterol oxidase with the sample is hydrogen peroxide.

(15) A reagent for measuring cholesterol in low-density lipoprotein contained in a sample, which comprises:
[a] a polyoxyethylene-polyoxyalkylene alkylaryl ether;
[b] one or more surfactants selected from the group consisting of a polyoxyethylene-polyoxyalkylene copolymer, a polyoxyethylene alkenyl ether, a polyoxyethylene branched alkyl ether, and a polyoxyethylene-polyoxyalkylene branched alkyl ether;
[c] one or more surfactants selected from the group consisting of a primary amine, a secondary amine, a tertiary amine, and a quaternary ammonium;
[d] a polyanion; and cholesterol ester hydrolase, an oxidized coenzyme, and cholesterol dehydrogenase.

(16) A reagent for measuring cholesterol in low-density lipoprotein contained in a sample, which comprises:
[a] a polyoxyethylene-polyoxyalkylene alkylaryl ether;
[b1] a polyoxyethylene-polyoxyalkylene copolymer;
[c] one or more surfactants selected from the group consisting of a primary amine, a secondary amine, a tertiary amine, and a quaternary ammonium;
[d] a polyanion; and
cholesterol ester hydrolase, an oxidized coenzyme, and cholesterol dehydrogenase.

(17) A reagent for measuring cholesterol in low-density lipoprotein contained in a sample, which comprises:
[a] a polyoxyethylene-polyoxyalkylene alkylaryl ether;
[b1] a polyoxyethylene-polyoxyalkylene copolymer;
[b2] one or more surfactants selected from the group consisting of a polyoxyethylene alkenyl ether, a polyoxyethylene branched alkyl ether, and a polyoxyethylene-polyoxyalkylene branched alkyl ether;
[c] one or more surfactants selected from the group consisting of a primary amine, a secondary amine, a tertiary amine, and a quaternary ammonium;
[d] a polyanion; and cholesterol ester hydrolase, an oxidized coenzyme, and cholesterol dehydrogenase.
(18) The reagent according to any one of (15) to (17) above, which further comprises a reagent for measuring the substance formed as a result of the reaction of the cholesterol ester hydrolase, the oxidized coenzyme, and the cholesterol dehydrogenase with the sample.
(19) The reagent according to (18) above, wherein the substance formed as a result of the reaction of the cholesterol ester hydrolase, the oxidized coenzyme, and the cholesterol dehydrogenase with the sample is a reduced coenzyme.
(20) The reagent according to any one of (10) to (19) above, wherein the quaternary ammonium salt is a trimethylalkylammonium salt or a benzyldimethylalkylammonium salt.
(21) The reagent according to any one of (10) to (19) above, wherein the tertiary amine is a dimethylalkylamine.
(22) A kit for measuring cholesterol in low-density lipoprotein contained in a sample, which comprises
a first reagent comprising at least one selected from the group consisting of:
[a] a polyoxyethylene-polyoxyalkylene alkylaryl ether;
[b] one or more surfactants selected from the group consisting of a polyoxyethylene-polyoxyalkylene copolymer, a polyoxyethylene alkenyl ether, a polyoxyethylene branched alkyl ether, and a polyoxyethylene-polyoxyalkylene branched alkyl ether;
[c] one or more surfactants selected from the group consisting of a primary amine, a secondary amine, a tertiary amine, and a quaternary ammonium;
[d] a polyanion; and
cholesterol ester hydrolase, and
a second reagent comprising cholesterol oxidase, wherein
each of the above described elements [a] to [d] and the cholesterol ester hydrolase is contained in either the first or second reagent, or in both of the first and second reagents.
(23) A kit for measuring cholesterol in low-density lipoprotein contained in a sample, which comprises
a first reagent comprising at least one selected from the group consisting of:
[a] a polyoxyethylene-polyoxyalkylene alkylaryl ether;
[b1] a polyoxyethylene-polyoxyalkylene copolymer;
[c] one or more surfactants selected from the group consisting of a primary amine, a secondary amine, a tertiary amine, and a quaternary ammonium;
[d] a polyanion; and cholesterol ester hydrolase, and
a second reagent comprising cholesterol oxidase, wherein
each of the above described elements [a] to [d] and the cholesterol ester hydrolase is contained in either the first or second reagent, or in both of the first and second reagents.
(24) A kit for measuring cholesterol in low-density lipoprotein contained in a sample, which comprises
a first reagent comprising at least one selected from the group consisting of:
[a] a polyoxyethylene-polyoxyalkylene alkylaryl ether;
[b1] a polyoxyethylene-polyoxyalkylene copolymer;
[b2] one or more surfactants selected from the group consisting of a polyoxyethylene alkenyl ether, a polyoxyethylene branched alkyl ether, and a polyoxyethylene-polyoxyalkylene branched alkyl ether;
[c] one or more surfactants selected from the group consisting of a primary amine, a secondary amine, a tertiary amine, and a quaternary ammonium;
[d] a polyanion; and
cholesterol ester hydrolase, and
a second reagent comprising cholesterol oxidase, wherein
each of the above described elements [a] to [d] and the cholesterol ester hydrolase is contained in either the first or second reagent, or in both of the first and second reagents.
(25) The kit according to any one of (22) to (24) above, which further comprises a reagent for measuring hydrogen peroxide in either the first or second reagent, or in both of the first and second reagents.
(26) A kit for measuring cholesterol in low-density lipoprotein contained in a sample, which comprises
a first reagent comprising at least one selected from the group consisting of:
[a] a polyoxyethylene-polyoxyalkylene alkylaryl ether;
[b] one or more surfactants selected from the group consisting of a polyoxyethylene-polyoxyalkylene copolymer, a polyoxyethylene alkenyl ether, a polyoxyethylene branched alkyl ether, and a polyoxyethylene-polyoxyalkylene branched alkyl ether;
[c] one or more surfactants selected from the group consisting of a primary amine, a secondary amine, a tertiary amine, and a quaternary ammonium;
[d] a polyanion;
an oxidized coenzyme; and cholesterol ester hydrolase, and
a second reagent comprising cholesterol dehydrogenase, wherein
each of the above described elements [a] to [d], the oxidized coenzyme, and the cholesterol ester hydrolase is contained in either the first or second reagent, or in both of the first and second reagents.
(27) A kit for measuring cholesterol in low-density lipoprotein contained in a sample, which comprises
a first reagent comprising at least one selected from the group consisting of:
[a] a polyoxyethylene-polyoxyalkylene alkylaryl ether;
[b1] a polyoxyethylene-polyoxyalkylene copolymer;
[c] one or more surfactants selected from the group consisting of a primary amine, a secondary amine, a tertiary amine, and a quaternary ammonium;
[d] a polyanion;
an oxidized coenzyme; and cholesterol ester hydrolase, and
a second reagent comprising cholesterol dehydrogenase, wherein
each of the above described elements [a] to [d], the oxidized coenzyme, and the cholesterol ester hydrolase is contained in either the first or second reagent, or in both of the first and second reagents.
(28) A kit for measuring cholesterol in low-density lipoprotein contained in a sample, which comprises
a first reagent comprising at least one selected from the group consisting of:
[a] a polyoxyethylene-polyoxyalkylene alkylaryl ether;
[b1] a polyoxyethylene-polyoxyalkylene copolymer;
[b2] one or more surfactants selected from the group consisting of a polyoxyethylene alkenyl ether, a polyoxyethylene branched alkyl ether, and a polyoxyethylene-polyoxyalkylene branched alkyl ether;

[c] one or more surfactants selected from the group consisting of a primary amine, a secondary amine, a tertiary amine, and a quaternary ammonium;
[d] a polyanion;
an oxidized coenzyme; and cholesterol ester hydrolase, and
a second reagent comprising cholesterol dehydrogenase, wherein
each of the above described elements [a] to [d], the oxidized coenzyme, and the cholesterol ester hydrolase is contained in either the first or second reagent, or in both of the first and second reagents.
(29) The kit according to any one of (26) to (28) above, which further comprises a reagent for measuring a reduced coenzyme in either the first or second reagent, or in both of the first and second reagents.
(30) The kit according to any one of (22) to (29) above, wherein the quaternary ammonium salt is a trimethyl alkyl ammonium salt or a benzyl dimethyl alkyl ammonium salt.
(31) The kit according to any one of (22) to (29) above, wherein the tertiary amine is a dimethyl alkyl amine.

Advantageous Effects of the Invention

According to the present invention, there are provided a method, a reagent, and a kit for simply and precisely measuring LDL-C contained in a sample.

DESCRIPTION OF EMBODIMENTS

The method for measuring LDL-C contained in a sample of the present invention is a method, which does not need operations to fractionate lipoproteins according to a physical method such as centrifugation. In addition, the method of the present invention is a method for measuring LDL-C contained in a sample without removing cholesterols in lipoproteins other than LDL contained in the sample prior to the measurement of LDL-C. Moreover, this is a method for measuring LDL-C contained in a sample without measuring cholesterols in lipoproteins other than LDL contained in the sample prior to the measurement of LDL-C.

One embodiment of the method of the present invention is a method, which comprises reacting a sample with (i) a combination of cholesterol ester hydrolase and cholesterol oxidase or (ii) a combination of cholesterol ester hydrolase, an oxidized coenzyme and cholesterol dehydrogenase in the presence of:
[a] a polyoxyethylene-polyoxyalkylene alkylaryl ether;
[b] one or more surfactants selected from the group consisting of a polyoxyethylene-polyoxyalkylene copolymer, a polyoxyethylene alkenyl ether, a polyoxyethylene branched alkyl ether, and a polyoxyethylene-polyoxyalkylene branched alkyl ether;
[c] one or more surfactants selected from the group consisting of a primary amine, a secondary amine, a tertiary amine, and a quaternary ammonium; and
[d] a polyanion, and measuring a substance formed or consumed in the reaction.

Another embodiment of the present invention relates to a method, which comprises reacting a sample with (i) a combination of cholesterol ester hydrolase and cholesterol oxidase or (ii) a combination of cholesterol ester hydrolase, an oxidized coenzyme and cholesterol dehydrogenase in the presence of:
[a] a polyoxyethylene-polyoxyalkylene alkylaryl ether;
[b1] a polyoxyethylene-polyoxyalkylene copolymer;
[c] one or more surfactants selected from the group consisting of a primary amine, a secondary amine, a tertiary amine, and a quaternary ammonium; and
[d] a polyanion, and
measuring a substance formed or consumed in the reaction.

A further embodiment of the present invention relates to a method, which comprises reacting a sample with (i) a combination of cholesterol ester hydrolase and cholesterol oxidase or (ii) a combination of cholesterol ester hydrolase, an oxidized coenzyme and cholesterol dehydrogenase in the presence of:
[a] a polyoxyethylene-polyoxyalkylene alkylaryl ether;
[b1] a polyoxyethylene-polyoxyalkylene copolymer;
[b2] one or more surfactants selected from the group consisting of a polyoxyethylene alkenyl ether, a polyoxyethylene branched alkyl ether, and a polyoxyethylene-polyoxyalkylene branched alkyl ether;
[c] one or more surfactants selected from the group consisting of a primary amine, a secondary amine, a tertiary amine, and a quaternary ammonium; and
[d] a polyanion, and
measuring a substance formed or consumed in the reaction.

All of the above described embodiments comprise:
[1] a step of carrying out the reaction of a sample with enzymes in the presence of surfactant(s) and a polyanion;
[2] a step of measuring a substance formed or consumed in the above described step [1];
[3] a step of correlating a calibration curve showing the relationship between the LDL-C concentration and information amount derived from the above described formed or consumed substance, which has previously been prepared using LDL-C having a known concentration, with the measurement value obtained in the above described step [2]; and
[4] a step of determining the concentration of LDL-C contained in the sample. Herein, enzymes to be reacted with the sample mean (i) a combination of cholesterol ester hydrolase and cholesterol oxidase, or (ii) a combination of cholesterol ester hydrolase, an oxidized coenzyme and cholesterol dehydrogenase.

In the method of the present invention, examples of a substance formed by the reaction of a sample with the enzymes include hydrogen peroxide and a reduced coenzyme. An example of a substance consumed by the reaction of a sample with the enzymes is an oxygen molecule. The formed hydrogen peroxide can be measured, for example, using a hydrogen peroxide electrode or the after-mentioned reagent for measuring hydrogen peroxide. The formed reduced coenzyme can be measured, for example, by a method of measuring the absorbance of such reduced coenzyme or the after-mentioned method using a reagent for measuring a reduced coenzyme. The wavelength used in the measurement of the absorbance of a reduced coenzyme is preferably 300 to 500 nm, more preferably 330 to 400 nm, and particularly preferably 340 nm. The consumed oxygen molecule can be measured, for example, using an oxygen electrode.

Examples of the sample used in the method of the present invention include whole blood, plasma and serum. Of these, plasma and serum are preferable. In addition, in the method of the present invention, not only a sample derived from a healthy subject, but a high TG sample having a high level of neutral fat (TG) can also be used.

The cholesterol ester hydrolase used in the present invention is not particularly limited, as long as it is an enzyme having the ability to hydrolyze cholesterol ester. Examples of such cholesterol ester hydrolase that can be used in the present invention include: cholesterol esterase and lipoprotein lipase, which are derived from animals, plants or microorganisms; and cholesterol esterase and lipoprotein lipase produced by genetic engineering methods.

As such cholesterol ester hydrolase, either an unmodified cholesterol ester hydrolase or a chemically modified cholesterol ester hydrolase can be used. In addition, commercially available ones can also be used.

Examples of such commercially available cholesterol ester hydrolase include cholesterol esterase (COE-311; manufactured by Toyobo Co., Ltd.), lipoprotein lipase (LPL-311; Toyobo Co., Ltd.), and cholesterol esterase III (CHEIII; manufactured by Amano Pharmaceutical Co., Ltd.). Moreover, two or more cholesterol ester hydrolases can also be used in combination in the present invention.

Examples of the groups modifying cholesterol ester hydrolase (a chemically modifying group) in the chemical modification of the enzyme include: a group comprising polyethylene glycol as a main component; a group comprising polypropylene glycol as a main component; a group having a copolymer of polypropylene glycol and polyethylene glycol; a group comprising water-soluble polysaccharide; a sulfopropyl group, a sulfobutyl group, a polyurethane group, and a group having a chelating function. Of these, a group comprising polyethylene glycol as a main component is preferable. Examples of such water-soluble polysaccharide include dextran, pullulan, and soluble starch.

Examples of the reagent for chemical modification of cholesterol ester hydrolase (chemical modifiers) include compounds, which have both the above chemically modifying group and a functional group or a structure capable of reacting with an amino group, a carboxyl group, a sulfhydryl group or the like in the enzyme. Examples of the functional group or the structure capable of reacting with an amino group in the enzyme include a carboxyl group, an active ester group (an N-hydroxysuccinimide group, etc.), an acid anhydride, an acid chloride, aldehyde, an epoxide group, 1,3-propane sultone, and 1,4-butane sultone. An example of the functional group or the structure capable of reacting with a carboxyl group in the enzyme is an amino group. Examples of the group or the structure having reactivity with a sulfhydryl group in the enzyme include a maleimide group, disulfide, and an $\alpha$-haloester (an $\alpha$-iodoester, etc.)

Commercially available chemically modifying reagents can also be used. Examples of such a commercially available chemically modifying reagent include: Sunbright VFM-4101, Sunbright ME-050AS and Sunbright DE-030AS (all of which are manufactured by NOF Corporation), which have a group comprising polyethylene glycol as a main component and an N-hydroxysuccinimide group; Sunbright AKM series (e.g. Sunbright AKM-1510, etc.), Sunbright ADM series and Sunbright ACM series (all of which are manufactured by NOF Corporation), which have a group comprising polyalkylene glycol as a main component and an acid anhydride structure; EPDX-3400 and M-EPDX-5000 (both of which are manufactured by Sheawater Polymers), which have a group comprising polyethylene glycol as a main component and an epoxide group; and diethylenetriamine-N,N,N',N'',N''-pentaacetic acid dianhydride (DTPA anhydride; manufactured by Dojindo Laboratories).

Cholesterol ester hydrolase can be chemically modified by the following method, for example. However, the chemical modification method is not limited thereto. First, cholesterol ester hydrolase is dissolved in a buffer with a pH value of 8.0 or greater (e.g. HEPES buffer), and a chemically modifying reagent is added at 0 to 55° C. in a molar amount of 0.01 to 500 times the molar amount of the cholesterol ester hydrolase to the obtained solution. The obtained solution is stirred for 5 minutes to 5 hours. In the enzyme reaction, not only this reaction solution as is, but also a solution, from which an unreacted chemically modifying reagent and the like are removed with the use of an ultrafilter membrane or the like, as necessary, can be used as a chemically modified cholesterol ester hydrolase.

The concentration of cholesterol ester hydrolase in the method of the present invention is not particularly limited, as long as it is a concentration, at which the measurement of LDL-C of the present invention can be carried out. The concentration of the cholesterol ester hydrolase in the reaction solution is generally 0.001 to 800 U/mL, and preferably 0.01 to 300 U/mL.

Cholesterol oxidase used in the present invention is not particularly limited, as long as it is an enzyme having ability to oxidize cholesterol and form hydrogen peroxide. Examples of such cholesterol oxidase that can be used in the present invention include: cholesterol oxidase derived from animals, plants or microorganisms; and cholesterol oxidase produced by genetic engineering methods. There can also be used commercially available products such as cholesterol oxidase (CHODI; manufactured by Kyowa Hakko Kogyo Co., Ltd.), cholesterol oxidase (CHODI; manufactured by KIKKOMAN Corporation), cholesterol oxidase (CHO-CE; manufactured by KIKKOMAN Corporation), and cholesterol oxidase (COO-321; manufactured by Toyobo Co., Ltd.). Moreover, two or more cholesterol oxidases can also be used in combination in the present invention.

As such cholesterol oxidase, either an unmodified enzyme or a chemically modified enzyme can be used. Such a chemically modified cholesterol oxidase can be produced, for example, by the above described chemical modification method using the above described chemically modifying reagent.

The concentration of cholesterol oxidase in the method of the present invention is not particularly limited, as long as it is a concentration, at which the measurement of LDL-C of the present invention can be carried out. The concentration of cholesterol oxidase in the reaction solution is generally 0.001 to 800 U/mL, and preferably 0.01 to 300 U/mL.

Cholesterol dehydrogenase used in the present invention is not particularly limited, as long as it is an enzyme having ability to oxidize cholesterol in the presence of an oxidized coenzyme and form a reduced coenzyme. Examples of such cholesterol dehydrogenase that can be used in the present invention include: cholesterol dehydrogenase derived from animals, plants or microorganisms; and cholesterol dehydrogenase produced by genetic engineering methods. Commercially available products such as cholesterol dehydrogenase "Amano" 5 (CHDH5; manufactured by Amano Enzyme Inc.) can also be used. Moreover, two or more cholesterol dehydrogenases can also be used in combination in the present invention. As such cholesterol dehydrogenase, either an unmodified enzyme or a chemically modified enzyme can be used. Such a chemically modified cholesterol dehydrogenase can be produced, for example, by the above described chemical modification method using the above described chemically modifying reagent.

The concentration of cholesterol dehydrogenase in the method of the present invention is not particularly limited, as long as it is a concentration, at which the measurement of LDL-C of the present invention can be carried out. The concentration of the cholesterol dehydrogenase in the reaction solution is generally 0.001 to 800 U/mL, and preferably 0.01 to 300 U/mL.

In the method of the present invention using cholesterol dehydrogenase, an oxidized coenzyme is used. Examples of the oxidized coenzyme include NAD, NADP, thio-NAD, and thio-NADP.

Examples of the alkyl in the polyoxyethylene-polyoxyalkylene alkylaryl ether (hereinafter abbreviated as POE-POA alkylaryl ether) used in the present invention include octyl, nonyl, decyl, and dodecyl. An example of aryl in the POE-POA alkylaryl ether is phenyl. The polymerization mode of POE-POA in the POE-POA alkylaryl ether is not particularly limited. Examples of the polymerization mode of POE-POA include block polymerization and random polymerization. Examples of such block polymerization include a diblock copolymer, a triblock copolymer, and a tetrablock copolymer. Examples of polyoxyalkylene (POA) in the POE-POA alkylaryl ether include those other than polyoxyethylene, such as polyoxypropylene and polyoxybutylene. Specific examples of the POE-POA alkylaryl ether include Emulgen L40 and the like (manufactured by Kao Corporation), and Acronecess KP189R, Acronecess KP189R-40 and Acronecess NP-189R (all of which are manufactured by NOF Corporation).

The polymerization mode of POE-POA in the polyoxyethylene-polyoxyalkylene copolymer (hereinafter abbreviated as a POE-POA copolymer) is not particularly limited. Examples of the polymerization mode of POE-POA include block polymerization and random polymerization. Examples of such block polymerization include a diblock copolymer, a triblock copolymer, and a tetrablock copolymer. Examples of polyoxyalkylene (POA) in the POE-POA copolymer include those other than polyoxyethylene, such as polyoxypropylene and polyoxybutylene. The molecular weight of polyoxyalkylene (POA) is 500 to 6000, and preferably 1500 to 4000. The molecular weight of the POE-POA copolymer is 500 to 12000, and preferably 1500 to 8000.

Specific examples of the POE-POA copolymer include Pluronic L-121, Pluronic P-103 and Pluronic F-108 (all of which are manufactured by Asahi Denka Kogyo K.K.), and Pronon B-204 and Acronecess B-208 (both of which are manufactured by NOF Corporation).

Examples of the alkenyl in the polyoxyethylene alkenyl ether (hereinafter abbreviated as a POE alkenyl ether) include alkenyl having 8 to 30 carbon atoms, such as octenyl, nonenyl, decenyl, undecenyl, dodecenyl, tridecenyl, tetradecenyl, pentadecenyl, hexadecenyl, heptadecenyl, octadecenyl, oleyl, nonadecenyl, eicosenyl, heneicosenyl, docosenyl, tricosenyl, tetracosenyl, pentacosenyl, hexacosenyl, heptacosenyl, octacosenyl, nonacosenyl, and triacontenyl. Of these, oleyl is preferable. The polymerization degree of oxyethylene in polyoxyethylene of the POE alkenyl ether is preferably 2 to 80, and more preferably 4 to 60. Specific examples of the POE alkenyl ether include BLAUNON EN-1530, BLAUNON EN-1540 and BLAUNON EN-1560 (manufactured by Aoki Oil Industrial Co., Ltd.), and Nonion E-215, Nonion E-230, Nonion E-235 and NOFABLE EAO-9020 (all of which are manufactured by NOF Corporation).

Examples of the branched alkyl in the polyoxyethylene branched alkyl ether (hereinafter abbreviated as a POE branched alkyl ether) include branched alkyl having 6 to 30 carbon atoms, such as isohexyl, isoheptyl, isooctyl, isononyl, isodecyl, isoundecyl, isododecyl, isotridecyl, isotetradecyl, isopentadecyl, isohexadecyl, isoheptadecyl, isooctadecyl, isononadecyl, isoicosyl, octyldodecyl, isoheneicosyl, isododecyl, isotricosyl, isotetracosyl, decyltetradecyl, isopentacosyl, isohexacosyl, dodecyltetradecyl, isoheptacosyl, isooctacosyl, isononacosyl, and isotriaconsyl. Of these, branched alkyl having 16 or more carbon atoms is preferable. Examples of such branched alkyl containing 16 or more carbon atoms include isohexadecyl, isoheptadecyl, isooctadecyl, isononadecyl, isoicosyl, octyldodecyl, isoheneicosyl, isododecyl, isotricosyl, isotetracosyl, decyltetradecyl, isopentacosyl, isohexacosyl, dodecyltetradecyl, isoheptacosyl, isooctacosyl, isononacosyl, and isotriaconsyl. The polymerization degree of oxyethylene in polyoxyethylene of the POE branched alkyl ether is preferably 2 to 80, and more preferably 4 to 60. Specific examples of the POE branched alkyl ether include Nonion IC235, Nonion IC230, Nonion IC235, Nonion OD225, Nonion OD230 and Nonion OD235 (all of which are manufactured by NOF Corporation), and EMALEX 1615, EMALEX 1625, EMALEX 1815, EMALEX 1820, EMALEX 1825, EMALEX OD-10, EMALEX OD-16, EMALEX OD-20, EMALEX OD-25, EMALEX OD-25JJ, EMALEX 2420 and EMALEX 2425 (all of which are manufactured by Nihon Emulsion Co., Ltd.).

Example of the branched alkyl in the polyoxyethylene-polyoxyalkylene branched alkyl ether (hereinafter abbreviated as a POE-POA branched alkyl ether) include branched alkyl having 6 to 30 carbon atoms, such as isohexyl, isoheptyl, isooctyl, isononyl, isodecyl, isoundecyl, isododecyl, isotridecyl, isotetradecyl, isopentadecyl, isohexadecyl, isoheptadecyl, isooctadecyl, isononadecyl, isoicosyl, octyldodecyl, isoheneicosyl, isododecyl, isotricosyl, isotetracosyl, decyltetradecyl, isopentacosyl, isohexacosyl, dodecyltetradecyl, isoheptacosyl, isooctacosyl, isononacosyl, and isotriaconsyl. Of these, isotetracosyl and decyltetradecyl are preferable. The polymerization mode of POE-POA in the POE-POA branched alkyl ether is not particularly limited. Examples of the polymerization mode of POE-POA include block polymerization and random polymerization. Examples of such block polymerization include a diblock copolymer, a triblock copolymer, and a tetrablock copolymer. Examples of polyoxyalkylene (POA) in the POE-POA branched alkyl ether include those other than polyoxyethylene, such as polyoxypropylene and polyoxybutylene. Specific examples of the POE-POA branched alkyl ether include Unilube MT-0620B, Unilube 50MT-2200B, Unilube 20MT-2000B and Unilube MIL-0822B (all of which are manufactured by NOF Corporation), and PEN-4620 and PEN-4630 (both of which are manufactured by Nikko Chemicals Co., Ltd.).

Examples of the quaternary ammonium salt include a trimethylalkylammonium salt and a benzyldimethylalkylammonium salt.

Examples of the alkyl in the trimethylalkylammonium salt include alkyl having 6 to 30 carbon atoms, such as hexyl, heptyl, octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl, and triaconsyl. Of these, alkyl having 8 to 20 carbon atoms is preferable. Examples of the alkyl having 8 to 20 carbon atoms include octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, and icosyl. Examples of the salt in the trimethylalkylammonium salt include a chloride, a bromide, an iodide, and a hydroxide. Examples of the trimethylalkylammonium salt include n-octyltrimethylammonium chloride, decyltrimethylammonium bromide, lauryltrimethylammonium bromide, n-dodecyltrimethylammonium chloride, n-tetradecyltrimethylammonium bromide, trimethyltetradecylammonium chloride, trimethylcetylammonium chloride, and trimethylstearylammonium chloride. Commercially available products of such a trimethylalkylammonium salt include Cation BB, Cation PB-40, Cation PB-300, Cation VB, Cation FB and Cation AT2-500 (all of which are manufactured by NOF Corporation).

Examples of the alkyl in the benzyldimethylalkylammonium salt include alkyl having 6 to 30 carbon atoms, such as hexyl, heptyl, octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl, and triaconsyl. Of these, alkyl having 8 to 20 carbon atoms is preferable. Examples of the alkyl having 8 to 20 carbon atoms include octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, and icosyl. Examples of the salt in the benzyl dimethyl alkyl ammonium salt include a chloride, a bromide, an iodide, and a hydroxide. Examples of the benzyldimethylalkylammonium salt include benzyldimethyldecylammonium bromide, benzyldimethyldecylammonium chloride, benzyldimethyllaurylammonium chloride, benzyldimethyltetradecylammonium chloride hydrate, benzylcetyldimethylammonium chloride hydrate, and benzyldimethylstearylammonium chloride hydrate. Commercially available products of such a benzyldimethylalkylammonium salt include Cation M2-100, Cation F2-35R, Cation F2-40E and Cation F2-50 (all of which are manufactured by NOF Corporation), and Morimin 10-B, Morimin 12-B and Morimin 14-B (all of which are manufactured by Morin Chemical Industries Co., Ltd.).

An example of the tertiary amine is dimethylalkylamine. Examples of alkyl in the dimethylalkylamine include alkyl having 6 to 30 carbon atoms, such as hexyl, heptyl, octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl, and triaconsyl. Of these, alkyl having 8 to 20 carbon atoms is preferable. Examples of the alkyl having 8 to 20 carbon atoms include octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, and icosyl. Specific examples of the dimethylalkylamine include dimethyloctylamine, dimethyldecylamine, dimethyldodecylamine, dimethyltetradecylamine, dimethylcetylamine, and dimethylstearylamine. Commercially available products of such a tertiary amine include Tertiary Amine BB, Tertiary Amine FB, and Tertiary Amine ABT (all of which are manufactured by NOF Corporation).

An example of the secondary amine is methylalkylamine. Examples of the alkyl in the methylalkylamine include alkyl having 6 to 30 carbon atoms, such as hexyl, heptyl, octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl, and triaconsyl. Of these, alkyl having 8 to 20 carbon atoms is preferable. Examples of the alkyl having 8 to 20 carbon atoms include octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, and icosyl. Specific examples of the methylalkylamine include methyloctylamine, methyldecylamine, methyldodecylamine, methyltetradecylamine, methylcetylamine, and methylstearylamine.

An example of the primary amine is alkylamine. Examples of the alkyl in the alkyl amine include alkyl having 6 to 30 carbon atoms, such as hexyl, heptyl, octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl, and triaconsyl. Of these, alkyl having 8 to 20 carbon atoms is preferable. Examples of the alkyl having 8 to 20 carbon atoms include octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, and icosyl. Specific examples of the alkylamine include octylamine, decylamine, dodecylamine, tetradecylamine, cetylamine, and stearylamine. Commercially available products of such an alkylamine include Amine BB, Amine PB, Amine MB, and Amine AB (all of which are manufactured by NOF Corporation).

In the method for measuring LDL-C of the present invention, when [a] a POE-POA alkylaryl ether and [b] one or more surfactants selected from the group consisting of a POE-POA copolymer, a POE alkenyl ether, a POE branched alkyl ether and a POE-POA branched alkyl ether (hereinafter referred to as a surfactant b) are used, the concentration of the POE-POA alkylaryl ether and the concentration of the surfactant b are not particularly limited, as long as they are concentrations, at which the method for measuring LDL-C of the present invention can be carried out. The concentration of each surfactant is generally 0.0001% to 20%, and preferably 0.001% to 5%.

In the method for measuring LDL-C of the present invention, when [a] a POE-POA alkylaryl ether and [b1] a POE-POA copolymer are used, the concentration of the POE-POA alkylaryl ether and the concentration of the POE-POA copolymer are not particularly limited, as long as they are concentrations, at which the method for measuring LDL-C of the present invention can be carried out. The concentration of each surfactant is generally 0.0001% to 20%, and preferably 0.001% to 5%.

In the method for measuring LDL-C of the present invention, when [a] a POE-POA alkylaryl ether, [b1] a POE-POA copolymer, and [b2] one or more surfactants selected from the group consisting of a POE alkenyl ether, a POE branched alkyl ether and a POE-POA branched alkyl ether (hereinafter referred to as a surfactant b2) are used, the concentrations of the POE-POA alkylaryl ether, POE-POA copolymer and surfactant b2 are not particularly limited, as long as they are concentrations, at which the method for measuring LDL-C of the present invention can be carried out. The concentration of each surfactant is generally 0.0001% to 20%, and preferably 0.001% to 5%.

The concentration of one or more surfactants selected from the group consisting of the primary amine, the secondary amine, the tertiary amine and the quaternary ammonium salt (hereinafter referred to as a surfactant c) is not particularly limited, as long as it is a concentration, at which the method for measuring LDL-C of the present invention can be carried out. The concentration is generally 0.00001% to 20%, and preferably 0.0001% to 5%.

Specific examples of the polyanion include dextran sulfate or a salt thereof, heparin or a salt thereof, phosphotungstic acid or a salt thereof, sulfonated cyclodextrin or a salt thereof, and sulfonated oligosaccharide or a salt thereof. Of these, dextran sulfate or a salt thereof is preferable. As such dextran sulfate, dextran sulfate having a molecular weight of 40,000, 80,000, 200,000, 500,000, 1,000,000 or 2,000,000 is used, for example. Examples of such sulfonated oligosaccharide include sulfonated agarose, sulfonated trehalose, and chondroitin sulfuric acid. Examples of such a salt include a sodium salt, a potassium salt, a lithium salt, an ammonium salt, and a magnesium salt. In addition, in the present invention, two or more polyanions can be used. The concentration of the polyanion used in the method for measuring LDL-C of the present invention is not particularly limited, as long as it is a concentration, at which the method for measuring LDL-C of the present invention can be carried out. It is generally 0.0005% to 10%, and preferably 0.005% to 1%.

The aqueous solvent used in the present invention is not particularly limited, as long as it is an aqueous solvent, with which the method for measuring LDL-C of the present invention can be carried out. Examples of such an aqueous solvent include deionized water, distilled water, and a buffer. Of these, a buffer is preferable.

The pH used in the method for measuring LDL-C of the present invention is not particularly limited, as long as it is a pH, at which the method for measuring LDL-C of the present invention can be carried out. It is pH 4 to 10, for example. When a buffer is used as an aqueous solvent, it is desired to use a buffering agent suitable for the determined pH. Examples of such a buffering agent used in a buffer include a Tris(hydroxymethyl)aminomethane buffer, a phosphate buffer, a borate buffer, and a Good's buffer.

Examples of such a Good's buffer include 2-morpholinoethanesulfonic acid (MES), bis(2-hydroxyethyl)iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxypropanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[tris(hydroxymethyl)methyl]glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO), and N-cyclohexyl-3-aminopropanesulfonic acid (CAPS).

The concentration of such a buffer is not particularly limited, as long as it is suitable for measurement. It is preferably 0.001 to 2.0 mol/L, and more preferably 0.005 to 1.0 mol/L.

The reaction temperature in the method for measuring LDL-C of the present invention is not particularly limited, as long as it is a temperature, at which the method for measuring LDL-C of the present invention can be carried out. It is preferably 10° C. to 50° C., and more preferably 30° C. to 40° C. The reaction temperature is generally set at 37° C. in a commonly used auto-analyzer.

The reaction time in the method for measuring LDL-C of the present invention is not particularly limited, as long as it is a time, at which the method for measuring LDL-C of the present invention can be carried out. It is preferably 1 to 60 minutes, and more preferably 2 to 30 minutes.

In the method for measuring LDL-C of the present invention, the measurement of LDL-C is carried out, for example, by measuring hydrogen peroxide or reduced coenzyme, which is formed as a result of the reaction. In addition, the measurement of LDL-C can also be carried out by measuring the amount of oxygen consumed in the reaction.

The amount of the formed hydrogen peroxide can be measured, for example, using a hydrogen peroxide electrode or a reagent for measuring hydrogen peroxide. The reagent for measuring hydrogen peroxide is a reagent for converting the formed hydrogen peroxide to a detectable substance. Examples of such detectable substances include a dye and a luminescent substance. Of these, a dye is preferable. When the detectable substance is a dye, the reagent for measuring hydrogen peroxide contains an oxidative coloring chromogen and a peroxidative substance such as a peroxidase. Examples of such an oxidative coloring chromogen include the aftermentioned oxidative coloring chromogens. When the detectable substance is a luminescent substance, the reagent for measuring hydrogen peroxide contains a chemiluminescent substance. Examples of such a chemiluminescent substance include luminol, isoluminol, lucigenin, and acridinium ester.

When a reagent containing an oxidative coloring chromogen or a peroxidative substance such as peroxidase is used as the reagent for measuring hydrogen peroxide, hydrogen peroxide reacts with the oxidative coloring chromogen in the presence of the peroxidative substance to form a dye. Hence, the hydrogen peroxide can be measured by measuring the thus formed dye. On the other hand, when a reagent for measuring hydrogen peroxide containing a chemiluminescent substance is used, hydrogen peroxide reacts with the chemiluminescent substance to form a photon. Hence, the hydrogen peroxide can be measured by measuring the thus formed photon.

Examples of the oxidative coloring chromogen include a leuco-type chromogen and an oxidative coupling-coloring chromogen. The leuco-type chromogen is a substance that is converted to a dye by itself in the presence of hydrogen peroxide and a peroxidative substance such as peroxidase. Specific examples include tetramethylbenzidine, o-phenylenediamine, 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), N-(carboxymethylaminocarbonyl)-4,4'-bis(dimethylamino)diphenylamine sodium salt (DA-64), 10-N-(carboxymethylaminocarbonyl)-3,7-bis(dimethylamino)-10H-phenothiazine sodium salt (DA-67), 4,4'-bis(dimethylamino)diphenylamine, and bis[3-bis(4-chlorophenyl)methyl-4-dimethylaminophenyl]amine (BCMA).

The oxidative coupling-coloring chromogen is a substance that forms a dye as a result of the oxidative coupling of two compounds in the presence of hydrogen peroxide and a peroxidative substance such as peroxidase. Examples of the combination of two compounds include a combination of a coupler and an aniline compound and a combination of a coupler and a phenol compound.

Examples of the coupler include 4-aminoantipyrine (4-AA) and 3-methyl-2-benzothiazolinonehydrazone.

Examples of the aniline compound include N-(3-sulfopropyl)aniline, N-ethyl-N-(2-hydroxy-3-sulfopropyl)-3-methylaniline (TOGS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-di(3-sulfopropyl)-3,5-dimethoxyaniline, N-ethyl-N-(3-sulfopropyl)-3-methoxyaniline, N-ethyl-N-(3-sulfopropyl) aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxyaniline, N-ethyl-N-(2-hydroxy-3-sulfopropyl) aniline, N-ethyl-N-(3-methylphenyl)-N'-succinylethylenediamine (EMSE), N-ethyl-N-(3-methylphenyl)-N'-acetylethylenediamine, N-ethyl-N-(2- hydroxy-3-sulfopropyl)-4-fluoro-3,5-dimethoxyaniline (F-DAOS), N-[2-(succinylamino)ethyl]-2-methoxy-5-methylaniline (MASE), and N-ethyl-N-[2-(succinylamino) ethyl]-2-methoxy-5-methylaniline (Et-MASE).

Examples of the phenol compound include phenol, 4-chlorophenol, 3-methylphenol, and 3-hydroxy-2,4,6-triiodobenzoic acid (HTIB).

The concentration of the peroxidative substance in the measurement of hydrogen peroxide is not particularly limited, as long as it is a concentration suitable for the measurement. When peroxidase is used as such a peroxidative substance, the concentration of the peroxidase is preferably 1 to 100 kU/L. Moreover, the concentration of an oxidative coloring chromogen is not particularly limited, as long as it is a concentration suitable for the measurement of hydrogen peroxide. It is preferably 0.01 to 10 g/L.

Examples of the method of measuring a reduced coenzyme include a method of measuring the absorbance of the formed reduced coenzyme and a method using a reagent for measuring a reduced coenzyme. The absorbance used in the method of measuring the absorbance of a reduced coenzyme is preferably 300 to 500 nm, more preferably 330 to 400 nm, and particularly preferably around 340 nm. The reagent for measuring a reduced coenzyme is a reagent for converting the formed reduced coenzyme to a detectable substance. An example of such a detectable substance is a dye. When the detectable substance is a dye, a reagent containing diaphorase, an electronic carrier and a reductive coloring chromogen is used as a reagent for measuring a reduced coenzyme, for example. An example of such an electronic carrier is 1-methoxy-5-methylphenadium methylsulfate. When a reagent containing diaphorase, an electronic carrier and a reductive coloring chromogen is used as a reagent for measuring a reduced coenzyme, a reduced coenzyme can be quantitatively determined by quantifying a dye formed as a result of the conversion of the reductive coloring chromogen.

Examples of the reductive coloring chromogen include 3-(4,5-dimethyl-2-thiazolyl)-2,5-diphenyl-2H-tetrazolium bromide (MTT), 2-(4-iodophenyl)-3-(4-nitrophenyl)-5-(2,4-disulfophenyl)-2H-tetrazolium monosodium salt (WST-1), and 2-(4-iodophenyl)-3-(2,4-dinitrophenyl)-5-(2,4-disulfophenyl)-2H-tetrazolium monosodium salt (WST-3).

(LDL-C-Measuring Reagent)

The reagent for measuring LDL-C of the present invention can be used in the method for measuring LDL-C of the present invention, and it is able to adopt a form of a kit, which is suitable for conservation, distribution and use. Examples of the kit for measuring LDL-C of the present invention include a two-reagent system kit and a three-reagent system kit. Of these, a two-reagent system kit consisting of a first reagent and a second reagent is preferable.

The reagent and kit for measuring LDL-C of the present invention can be either in a state in which they are freeze-dried or in a state in which they are dissolved in an aqueous solvent. When LDL-C contained in a sample is measured using a reagent or a kit which is in a freeze-dried state, the reagent is dissolved in an aqueous solvent before use. As such an aqueous solvent, those as described above are used, for example.

In the reagent and kit for measuring LDL-C of the present invention, the above described cholesterol ester hydrolase, cholesterol oxidase, oxidized coenzyme, cholesterol dehydrogenase, POE-POA alkylaryl ether, POE-POA copolymer, POE alkenyl ether, POE branched alkyl ether, POE-POA branched alkyl ether, quaternary ammonium salt, tertiary amine, secondary amine, primary amine, polyanion, a reagent for measuring hydrogen peroxide, and a reagent for measuring a reduced coenzyme can be used.

In a kit for measuring LDL-C, which is a two-reagent system kit consisting of a first reagent and a second reagent, cholesterol ester hydrolase is contained in either or both of the first and second reagents. In a two-reagent system kit for measuring LDL-C, which uses cholesterol ester hydrolase and cholesterol oxidase, the cholesterol oxidase is not contained in the first reagent, but is contained in the second reagent. In addition, in a two-reagent system kit for measuring LDL-C, which uses cholesterol ester hydrolase, cholesterol dehydrogenase and oxidized coenzyme, cholesterol dehydrogenase is not contained in the first reagent but is contained in the second reagent, whereas the oxidized coenzyme is contained in either or both of the first and second reagents.

The POE-POA aryl ether can be contained in either or both of the first and second reagents. An embodiment in which the POE-POA aryl ether is contained in the second reagent is preferable.

The surfactant b is contained in either or both of the first and second reagents.

The quaternary ammonium salt is contained in either or both of the first and second reagents.

The tertiary amine is contained in either or both of the first and second reagents.

The secondary amine is contained in either or both of the first and second reagents.

The primary amine is contained in either or both of the first and second reagents.

The polyanion is contained in either or both of the first and second reagents.

The reagent for measuring hydrogen peroxide can be contained in either or both of the first and second reagents. When the reagent contains an oxidative coupling chromogen, an embodiment in which each of the two compounds of the oxidative coupling chromogen, namely, a coupler and an aniline compound, or a coupler and a phenol compound, is contained in different reagents separately, is preferable.

The reagent for measuring a reduced coenzyme can be contained in either or both of the first and second reagents. The reagent for measuring a reduced coenzyme is preferably contained in both of the first and second reagents.

The reagent and kit for measuring LDL-C of the present invention can further comprise an aqueous solvent, a stabilizer, an antiseptic, an affecting substance-removing agent, a reaction promoter and the like, as necessary. As such an aqueous solvent, those as described above are used. Examples of the stabilizer include ethylenediamine tetraacetic acid (EDTA), sucrose, and calcium chloride. Examples of the antiseptic include sodium azide and an antibiotic. An example of the affecting substance-removing agent is ascorbate oxidase for removing the influence of ascorbic acid. Examples of the reaction promoter include enzymes such as colipase and phospholipase, and salts such as sodium sulfate and sodium chloride.

Hereinafter, specific embodiments of the reagent for measuring LDL-C of the present invention will be described. However, the reagent for measuring LDL-C of the present invention is not limited to these embodiments.

Reagent 1

A reagent comprising a POE-POA alkylaryl ether, surfactant b, surfactant c, a polyanion, cholesterol ester hydrolase and cholesterol oxidase.

Reagent 2

A reagent comprising a POE-POA alkylaryl ether, surfactant b, surfactant c, a polyanion, cholesterol ester hydrolase, cholesterol oxidase and a reagent for measuring hydrogen peroxide.

Reagent 3

A reagent comprising a POE-POA alkylaryl ether, a POE-POA copolymer, surfactant c, a polyanion, cholesterol ester hydrolase and cholesterol oxidase.

Reagent 4

A reagent comprising a POE-POA alkylaryl ether, a POE-POA copolymer, surfactant c, a polyanion, cholesterol ester hydrolase, cholesterol oxidase and a reagent for measuring hydrogen peroxide.

Reagent 5

A reagent comprising a POE-POA alkylaryl ether, a POE-POA copolymer, surfactant b2, surfactant c, a polyanion, cholesterol ester hydrolase and cholesterol oxidase.

Reagent 6

A reagent comprising a POE-POA alkylaryl ether, a POE-POA copolymer, surfactant b2, surfactant c, a polyanion, cholesterol ester hydrolase, cholesterol oxidase and a reagent for measuring hydrogen peroxide.

Reagent 7

A reagent comprising a POE-POA alkylaryl ether, surfactant b, surfactant c, a polyanion, cholesterol ester hydrolase, an oxidized coenzyme and cholesterol dehydrogenase.

Reagent 8

A reagent comprising a POE-POA alkylaryl ether, surfactant b, surfactant c, a polyanion, cholesterol ester hydrolase, an oxidized coenzyme, cholesterol dehydrogenase and a reagent for measuring a reduced coenzyme.

Reagent 9

A reagent comprising a POE-POA alkylaryl ether, a POE-POA copolymer, surfactant c, a polyanion, cholesterol ester hydrolase, an oxidized coenzyme and cholesterol dehydrogenase.

Reagent 10

A reagent comprising a POE-POA alkylaryl ether, a POE-POA copolymer, surfactant c, a polyanion, cholesterol ester hydrolase, an oxidized coenzyme, cholesterol dehydrogenase and a reagent for measuring a reduced coenzyme.

Reagent 11

A reagent comprising a POE-POA alkylaryl ether, a POE-POA copolymer, surfactant b2, surfactant c, a polyanion, cholesterol ester hydrolase, an oxidized coenzyme and cholesterol dehydrogenase.

Reagent 12

A reagent comprising a POE-POA alkylaryl ether, a POE-POA copolymer, surfactant b2, surfactant c, a polyanion, cholesterol ester hydrolase, an oxidized coenzyme, cholesterol dehydrogenase and a reagent for measuring a reduced coenzyme.

Hereinafter, specific embodiments of the kit for measuring LDL-C of the present invention will be described. However, the kit for measuring LDL-C of the present invention is not limited to these embodiments.

Kit 1

First Reagent

A polyanion

Second Reagent

A POE-POA alkylaryl ether, surfactant b, surfactant c, cholesterol ester hydrolase and cholesterol oxidase Kit 2

First Reagent

A polyanion and cholesterol ester hydrolase

Second Reagent

A POE-POA alkylaryl ether, surfactant b, surfactant c and cholesterol oxidase

Kit 3

First Reagent

A polyanion and cholesterol ester hydrolase

Second Reagent

A POE-POA alkylaryl ether, surfactant b, surfactant c, cholesterol ester hydrolase and cholesterol oxidase Kit 4

First Reagent

A polyanion and a reagent for measuring hydrogen peroxide

Second Reagent

A POE-POA alkylaryl ether, surfactant b, surfactant c, a reagent for measuring hydrogen peroxide, cholesterol ester hydrolase and cholesterol oxidase Kit 5

First Reagent

A polyanion, a reagent for measuring hydrogen peroxide and cholesterol ester hydrolase Second Reagent A POE-POA alkylaryl ether, surfactant b, surfactant c, a reagent for measuring hydrogen peroxide, and cholesterol oxidase Kit 6

First Reagent

A polyanion, a reagent for measuring hydrogen peroxide and cholesterol ester hydrolase Second Reagent A POE-POA alkylaryl ether, surfactant b, surfactant c, a reagent for measuring hydrogen peroxide, cholesterol ester hydrolase and cholesterol oxidase Kit 7

First Reagent

Polyanion

Second Reagent

A POE-POA alkylaryl ether, a POE-POA copolymer, surfactant c, cholesterol ester hydrolase and cholesterol oxidase Kit 8

First Reagent

A polyanion and cholesterol ester hydrolase

Second Reagent

A POE-POA alkylaryl ether, a POE-POA copolymer, surfactant c and cholesterol oxidase Kit 9

First Reagent

A polyanion and cholesterol ester hydrolase

Second Reagent

A POE-POA alkylaryl ether, a POE-POA copolymer, surfactant c, cholesterol ester hydrolase and cholesterol oxidase Kit 10

First Reagent

A polyanion and a reagent for measuring hydrogen peroxide

Second Reagent

A POE-POA alkylaryl ether, a POE-POA copolymer, surfactant c, a reagent for measuring hydrogen peroxide, cholesterol ester hydrolase and cholesterol oxidase Kit 11
First Reagent
  A polyanion, a reagent for measuring hydrogen peroxide and cholesterol ester hydrolase
Second Reagent
  A POE-POA alkylaryl ether, a POE-POA copolymer, surfactant c, a reagent for measuring hydrogen peroxide and cholesterol oxidase Kit 12
First Reagent
  A polyanion, a reagent for measuring hydrogen peroxide and cholesterol ester hydrolase
Second Reagent
  A POE-POA alkylaryl ether, a POE-POA copolymer, surfactant c, a reagent for measuring hydrogen peroxide, cholesterol ester hydrolase and cholesterol oxidase Kit 13
First Reagent
  A polyanion
Second Reagent
  A POE-POA alkylaryl ether, a POE-POA copolymer, surfactant b2, surfactant c, cholesterol ester hydrolase and cholesterol oxidase Kit 14
First Reagent
  A polyanion and cholesterol ester hydrolase
Second Reagent
  A POE-POA alkylaryl ether, a POE-POA copolymer, surfactant b2, surfactant c and cholesterol oxidase Kit 15
First Reagent
  A polyanion and cholesterol ester hydrolase
Second Reagent
  A POE-POA alkylaryl ether, a POE-POA copolymer, surfactant b2, surfactant c, cholesterol ester hydrolase and cholesterol oxidase Kit 16
First Reagent
  A polyanion and a reagent for measuring hydrogen peroxide
Second Reagent
  A POE-POA alkylaryl ether, a POE-POA copolymer, surfactant b2, surfactant c, a reagent for measuring hydrogen peroxide, cholesterol ester hydrolase and cholesterol oxidase Kit 17
First Reagent
  A polyanion, a reagent for measuring hydrogen peroxide and cholesterol ester hydrolase
Second Reagent
  A POE-POA alkylaryl ether, a POE-POA copolymer, surfactant b2, surfactant c, a reagent for measuring hydrogen peroxide and cholesterol oxidase Kit 18
First Reagent
  A polyanion, a reagent for measuring hydrogen peroxide and cholesterol ester hydrolase
Second Reagent
  A POE-POA alkylaryl ether, a POE-POA copolymer, surfactant b2, surfactant c, a reagent for measuring hydrogen peroxide, cholesterol ester hydrolase and cholesterol oxidase Kit 19
First Reagent
  A polyanion and a POE-POA copolymer
Second Reagent
  A POE-POA alkylaryl ether, surfactant c, cholesterol ester hydrolase and cholesterol oxidase Kit 20
First Reagent
  A polyanion, a POE-POA copolymer and cholesterol ester hydrolase
Second Reagent
  A POE-POA alkylaryl ether, surfactant c and cholesterol oxidase Kit 21
First Reagent
  A polyanion, a POE-POA copolymer and cholesterol ester hydrolase
Second Reagent
  A POE-POA alkylaryl ether, surfactant c, cholesterol ester hydrolase and cholesterol oxidase Kit 22
First Reagent
  A polyanion, a POE-POA copolymer and a reagent for measuring hydrogen peroxide
Second Reagent
  A POE-POA alkylaryl ether, surfactant c, a reagent for measuring hydrogen peroxide, cholesterol ester hydrolase and cholesterol oxidase Kit 23
First Reagent
  A polyanion, a POE-POA copolymer, a reagent for measuring hydrogen peroxide and cholesterol ester hydrolase
Second Reagent
  A POE-POA alkylaryl ether, surfactant c, a reagent for measuring hydrogen peroxide, and cholesterol oxidase Kit 24
First Reagent
  A polyanion, a POE-POA copolymer, a reagent for measuring hydrogen peroxide, and cholesterol ester hydrolase
Second Reagent
  A POE-POA alkylaryl ether, surfactant c, a reagent for measuring hydrogen peroxide, cholesterol ester hydrolase and cholesterol oxidase Kit 25
First Reagent
  A polyanion and a POE-POA copolymer
Second Reagent
  A POE-POA alkylaryl ether, a POE-POA copolymer, surfactant c, cholesterol ester hydrolase and cholesterol oxidase Kit 26
First Reagent
  A polyanion, a POE-POA copolymer and cholesterol ester hydrolase
Second Reagent
  A POE-POA alkylaryl ether, a POE-POA copolymer, surfactant c and cholesterol oxidase Kit 27
First Reagent
  A polyanion, a POE-POA copolymer and cholesterol ester hydrolase
Second Reagent
  A POE-POA alkylaryl ether, a POE-POA copolymer, surfactant c, cholesterol ester hydrolase and cholesterol oxidase Kit 28
First Reagent
  A polyanion, a POE-POA copolymer and a reagent for measuring hydrogen peroxide
Second Reagent
  A POE-POA alkylaryl ether, a POE-POA copolymer, surfactant c, a reagent for measuring hydrogen peroxide, cholesterol ester hydrolase and cholesterol oxidase Kit 29
First Reagent
    A polyanion, a POE-POA copolymer, a reagent for measuring hydrogen peroxide, and cholesterol ester hydrolase
Second Reagent
    A POE-POA alkylaryl ether, a POE-POA copolymer, surfactant c, a reagent for measuring hydrogen peroxide, and cholesterol oxidase
Kit 30
First Reagent
    A polyanion, a POE-POA copolymer, a reagent for measuring hydrogen peroxide, and cholesterol ester hydrolase
Second Reagent
    A POE-POA alkylaryl ether, a POE-POA copolymer, surfactant c, a reagent for measuring hydrogen peroxide, cholesterol ester hydrolase and cholesterol oxidase
Kit 31
First Reagent
    A polyanion and a POE-POA copolymer
Second Reagent
    A POE-POA alkylaryl ether, surfactant b2, surfactant c, cholesterol ester hydrolase and cholesterol oxidase
Kit 32
First Reagent
    A polyanion, a POE-POA copolymer and cholesterol ester hydrolase
Second Reagent
    A POE-POA alkylaryl ether, surfactant b2, surfactant c and cholesterol oxidase
Kit 33
First Reagent
    A polyanion, a POE-POA copolymer and cholesterol ester hydrolase
Second Reagent
    A POE-POA alkylaryl ether, surfactant b2, surfactant c, cholesterol ester hydrolase and cholesterol oxidase
Kit 34
First Reagent
    A polyanion, a POE-POA copolymer and a reagent for measuring hydrogen peroxide
Second Reagent
    A POE-POA alkylaryl ether, surfactant b2, surfactant c, a reagent for measuring hydrogen peroxide, cholesterol ester hydrolase and cholesterol oxidase
Kit 35
First Reagent
    A polyanion, a POE-POA copolymer, a reagent for measuring hydrogen peroxide, and cholesterol ester hydrolase
Second Reagent
    A POE-POA alkylaryl ether, surfactant b2, surfactant c, a reagent for measuring hydrogen peroxide, and cholesterol oxidase
Kit 36
First Reagent
    Polyanion, a POE-POA copolymer, a reagent for measuring hydrogen peroxide, and cholesterol ester hydrolase
Second Reagent
    A POE-POA alkylaryl ether, surfactant b2, surfactant c, a reagent for measuring hydrogen peroxide, cholesterol ester hydrolase and cholesterol oxidase
Kit 37
First Reagent
    A polyanion and surfactant b
Second Reagent
    A POE-POA alkylaryl ether, surfactant c, cholesterol ester hydrolase and cholesterol oxidase
Kit 38
First Reagent
    A polyanion, surfactant b and cholesterol ester hydrolase
Second Reagent
    A POE-POA alkylaryl ether, surfactant c and cholesterol oxidase
Kit 39
First Reagent
    A polyanion, surfactant b and cholesterol ester hydrolase
Second Reagent
    A POE-POA alkylaryl ether, surfactant c, cholesterol ester hydrolase and cholesterol oxidase
Kit 40
First Reagent
    A polyanion, surfactant b and a reagent for measuring hydrogen peroxide
Second Reagent
    A POE-POA alkylaryl ether, surfactant c, a reagent for measuring hydrogen peroxide, cholesterol ester hydrolase and cholesterol oxidase
Kit 41
First Reagent
    A polyanion, surfactant b, a reagent for measuring hydrogen peroxide, and cholesterol ester hydrolase
Second Reagent
    A POE-POA alkylaryl ether, surfactant c, a reagent for measuring hydrogen peroxide, and cholesterol oxidase
Kit 42
First Reagent
    A polyanion, surfactant b, a reagent for measuring hydrogen peroxide, and cholesterol ester hydrolase
Second Reagent
    A POE-POA alkylaryl ether, surfactant c, a reagent for measuring hydrogen peroxide, cholesterol ester hydrolase and cholesterol oxidase
Kit 43
First Reagent
    A polyanion and surfactant b2
Second Reagent
    A POE-POA alkylaryl ether, a POE-POA copolymer, surfactant c, cholesterol ester hydrolase and cholesterol oxidase
Kit 44
First Reagent
    A polyanion, surfactant b2 and cholesterol ester hydrolase
Second Reagent
    A POE-POA alkylaryl ether, a POE-POA copolymer, surfactant c and cholesterol oxidase
Kit 45
First Reagent
    A polyanion, surfactant b2 and cholesterol ester hydrolase
Second Reagent
    A POE-POA alkylaryl ether, a POE-POA copolymer, surfactant c, cholesterol ester hydrolase and cholesterol oxidase
Kit 46
First Reagent
    A polyanion, surfactant b2 and a reagent for measuring hydrogen peroxide
Second Reagent
    A POE-POA alkylaryl ether, a POE/POA copolymer, surfactant c, a reagent for measuring hydrogen peroxide, cholesterol ester hydrolase and cholesterol oxidase
Kit 47
First Reagent
    A polyanion, surfactant b2, a reagent for measuring hydrogen peroxide, and cholesterol ester hydrolase Second Reagent
   A POE-POA alkylaryl ether, a POE-POA copolymer, surfactant c, a reagent for measuring hydrogen peroxide, and cholesterol oxidase
   Kit 48
First Reagent
   A polyanion, surfactant b2, a reagent for measuring hydrogen peroxide, and cholesterol ester hydrolase
Second Reagent
   A POE-POA alkylaryl ether, a POE-POA copolymer, surfactant c, a reagent for measuring hydrogen peroxide, cholesterol ester hydrolase and cholesterol oxidase
   Kit 49
First Reagent
   A polyanion and surfactant b
Second Reagent
   A POE-POA alkylaryl ether, surfactant b, surfactant c, cholesterol ester hydrolase and cholesterol oxidase
   Kit 50
First Reagent
   A polyanion, surfactant b and cholesterol ester hydrolase
Second Reagent
   A POE-POA alkylaryl ether, surfactant b, surfactant c and cholesterol oxidase
   Kit 51
First Reagent
   A polyanion, surfactant b and cholesterol ester hydrolase
Second Reagent
   A POE-POA alkylaryl ether, surfactant b, surfactant c, cholesterol ester hydrolase and cholesterol oxidase
   Kit 52
First Reagent
   A polyanion, surfactant b and a reagent for measuring hydrogen peroxide
Second Reagent
   A POE-POA alkylaryl ether, surfactant b, surfactant c, a reagent for measuring hydrogen peroxide, cholesterol ester hydrolase and cholesterol oxidase
   Kit 53
First Reagent
   A polyanion, surfactant b, a reagent for measuring hydrogen peroxide, and cholesterol ester hydrolase
Second Reagent
   A POE-POA alkylaryl ether, surfactant b, surfactant c, a reagent for measuring hydrogen peroxide, and cholesterol oxidase
   Kit 54
First Reagent
   A polyanion, surfactant b, a reagent for measuring hydrogen peroxide, and cholesterol ester hydrolase
Second Reagent
   A POE-POA alkylaryl ether, surfactant b, surfactant c, a reagent for measuring hydrogen peroxide, cholesterol ester hydrolase and cholesterol oxidase
   Kit 55
First Reagent
   A polyanion and an oxidized coenzyme
Second Reagent
   A POE-POA alkylaryl ether, surfactant b, surfactant c, cholesterol ester hydrolase and cholesterol dehydrogenase
   Kit 56
First Reagent
   A polyanion, an oxidized coenzyme and cholesterol ester hydrolase
Second Reagent
   A POE-POA alkylaryl ether, surfactant b, surfactant c and cholesterol dehydrogenase
   Kit 57
First Reagent
   A polyanion, an oxidized coenzyme and cholesterol ester hydrolase
Second Reagent
   A POE-POA alkylaryl ether, surfactant b, surfactant c, cholesterol ester hydrolase and cholesterol dehydrogenase
   Kit 58
First Reagent
   A polyanion, an oxidized coenzyme and a reagent for measuring a reduced coenzyme
Second Reagent
   A POE-POA alkylaryl ether, surfactant b, surfactant c, a reagent for measuring a reduced coenzyme, cholesterol ester hydrolase and cholesterol dehydrogenase
   Kit 59
First Reagent
   A polyanion, an oxidized coenzyme, a reagent for measuring a reduced coenzyme, and cholesterol ester hydrolase
Second Reagent
   A POE-POA alkylaryl ether, surfactant b, surfactant c, a reagent for measuring a reduced coenzyme, and cholesterol dehydrogenase
   Kit 60
First Reagent
   A polyanion, an oxidized coenzyme, a reagent for measuring a reduced coenzyme, and cholesterol ester hydrolase
Second Reagent
   A POE-POA alkylaryl ether, surfactant b, surfactant c, a reagent for measuring a reduced coenzyme, cholesterol ester hydrolase and cholesterol dehydrogenase
   Kit 61
First Reagent
   A polyanion and an oxidized coenzyme
Second Reagent
   A POE-POA alkylaryl ether, a POE-POA copolymer, surfactant c, cholesterol ester hydrolase and cholesterol dehydrogenase
   Kit 62
First Reagent
   A polyanion, an oxidized coenzyme and cholesterol ester hydrolase
Second Reagent
   A POE-POA alkylaryl ether, a POE-POA copolymer, surfactant c and cholesterol dehydrogenase
   Kit 63
First Reagent
   A polyanion, an oxidized coenzyme and cholesterol ester hydrolase
Second Reagent
   A POE-POA alkylaryl ether, a POE-POA copolymer, surfactant c, cholesterol ester hydrolase and cholesterol dehydrogenase
   Kit 64
First Reagent
   A polyanion, an oxidized coenzyme and a reagent for measuring a reduced coenzyme
Second Reagent
   A POE-POA alkylaryl ether, a POE-POA copolymer, surfactant c, a reagent for measuring a reduced coenzyme, cholesterol ester hydrolase and cholesterol dehydrogenase Kit 65
First Reagent
A polyanion, an oxidized coenzyme, a reagent for measuring a reduced coenzyme, and cholesterol ester hydrolase
Second Reagent
A POE-POA alkylaryl ether, a POE-POA copolymer, surfactant c, a reagent for measuring a reduced coenzyme, and cholesterol dehydrogenase Kit 66
First Reagent
A polyanion, an oxidized coenzyme, a reagent for measuring a reduced coenzyme, and cholesterol ester hydrolase
Second Reagent
A POE-POA alkylaryl ether, a POE-POA copolymer, surfactant c, a reagent for measuring a reduced coenzyme, cholesterol ester hydrolase and cholesterol dehydrogenase Kit 67
First Reagent
A polyanion and an oxidized coenzyme
Second Reagent
A POE-POA alkylaryl ether, a POE-POA copolymer, surfactant b2, surfactant c, cholesterol ester hydrolase and cholesterol dehydrogenase Kit 68
First Reagent
A polyanion, an oxidized coenzyme and cholesterol ester hydrolase
Second Reagent
A POE-POA alkylaryl ether, a POE-POA copolymer, surfactant b2, surfactant c and cholesterol dehydrogenase Kit 69
First Reagent
A polyanion, an oxidized coenzyme and cholesterol ester hydrolase
Second Reagent
A POE-POA alkylaryl ether, a POE-POA copolymer, surfactant b2, surfactant c, cholesterol ester hydrolase and cholesterol dehydrogenase Kit 70
First Reagent
A polyanion, an oxidized coenzyme and a reagent for measuring a reduced coenzyme
Second Reagent
A POE-POA alkylaryl ether, a POE-POA copolymer, surfactant b2, surfactant c, a reagent for measuring a reduced coenzyme, cholesterol ester hydrolase and cholesterol dehydrogenase Kit 71
First Reagent
A polyanion, an oxidized coenzyme, a reagent for measuring a reduced coenzyme, and cholesterol ester hydrolase
Second Reagent
A POE-POA alkylaryl ether, a POE-POA copolymer, surfactant b2, surfactant c, a reagent for measuring a reduced coenzyme, and cholesterol dehydrogenase Kit 72
First Reagent
A polyanion, an oxidized coenzyme, a reagent for measuring a reduced coenzyme, and cholesterol ester hydrolase
Second Reagent
A POE-POA alkylaryl ether, a POE-POA copolymer, surfactant b2, surfactant c, a reagent for measuring a reduced coenzyme, cholesterol ester hydrolase and cholesterol dehydrogenase Kit 73
First Reagent
A polyanion, an oxidized coenzyme and a POE-POA copolymer
Second Reagent
A POE-POA alkylaryl ether, surfactant c, cholesterol ester hydrolase and cholesterol dehydrogenase Kit 74
First Reagent
A polyanion, an oxidized coenzyme, a POE-POA copolymer and cholesterol ester hydrolase
Second Reagent
A POE-POA alkylaryl ether, surfactant c and cholesterol dehydrogenase Kit 75
First Reagent
A polyanion, an oxidized coenzyme, a POE-POA copolymer and cholesterol ester hydrolase
Second Reagent
A POE-POA alkylaryl ether, surfactant c, cholesterol ester hydrolase and cholesterol dehydrogenase Kit 76
First Reagent
A polyanion, an oxidized coenzyme, a POE-POA copolymer and a reagent for measuring a reduced coenzyme
Second Reagent
A POE-POA alkylaryl ether, surfactant c, a reagent for measuring a reduced coenzyme, cholesterol ester hydrolase and cholesterol dehydrogenase Kit 77
First Reagent
A polyanion, an oxidized coenzyme, a POE-POA copolymer, a reagent for measuring a reduced coenzyme, and cholesterol ester hydrolase
Second Reagent
A POE-POA alkylaryl ether, surfactant c, a reagent for measuring a reduced coenzyme, and cholesterol dehydrogenase Kit 78
First Reagent
A polyanion, an oxidized coenzyme, a POE-POA copolymer, a reagent for measuring a reduced coenzyme, and cholesterol ester hydrolase
Second Reagent
A POE-POA alkylaryl ether, surfactant c, a reagent for measuring a reduced coenzyme, cholesterol ester hydrolase and cholesterol dehydrogenase Kit 79
First Reagent
A polyanion, an oxidized coenzyme and a POE-POA copolymer
Second Reagent
A POE-POA alkylaryl ether, a POE-POA copolymer, surfactant c, cholesterol ester hydrolase and cholesterol dehydrogenase Kit 80
First Reagent
A polyanion, an oxidized coenzyme, a POE-POA copolymer and cholesterol ester hydrolase
Second Reagent
A POE-POA alkylaryl ether, a POE-POA copolymer, surfactant c and cholesterol dehydrogenase Kit 81
First Reagent
 A polyanion, an oxidized coenzyme, a POE-POA copolymer and cholesterol ester hydrolase
Second Reagent
 A POE-POA alkylaryl ether, a POE-POA copolymer, surfactant c, cholesterol ester hydrolase and cholesterol dehydrogenase Kit 82
First Reagent
 A polyanion, an oxidized coenzyme, a POE-POA copolymer and a reagent for measuring a reduced coenzyme
Second Reagent
 A POE-POA alkylaryl ether, a POE-POA copolymer, surfactant c, a reagent for measuring a reduced coenzyme, cholesterol ester hydrolase and cholesterol dehydrogenase Kit 83
First Reagent
 A polyanion, an oxidized coenzyme, a POE-POA copolymer, a reagent for measuring a reduced coenzyme, and cholesterol ester hydrolase
Second Reagent
 A POE-POA alkylaryl ether, a POE-POA copolymer, surfactant c, a reagent for measuring a reduced coenzyme, and cholesterol dehydrogenase Kit 84
First Reagent
 A polyanion, an oxidized coenzyme, a POE-POA copolymer, a reagent for measuring a reduced coenzyme, and cholesterol ester hydrolase
Second Reagent
 A POE-POA alkylaryl ether, a POE-POA copolymer, surfactant c, a reagent for measuring a reduced coenzyme, cholesterol ester hydrolase and cholesterol dehydrogenase Kit 85
First Reagent
 A polyanion, an oxidized coenzyme and a POE-POA copolymer
Second Reagent
 A POE-POA alkylaryl ether, surfactant b2, surfactant c, cholesterol ester hydrolase and cholesterol dehydrogenase Kit 86
First Reagent
 A polyanion, an oxidized coenzyme, a POE-POA copolymer and cholesterol ester hydrolase
Second Reagent
 A POE-POA alkylaryl ether, surfactant b2, surfactant c and cholesterol dehydrogenase Kit 87
First Reagent
 A polyanion, an oxidized coenzyme, a POE-POA copolymer and cholesterol ester hydrolase
Second Reagent
 A POE-POA alkylaryl ether, surfactant b2, surfactant c, cholesterol ester hydrolase and cholesterol dehydrogenase Kit 88
First Reagent
 A polyanion, an oxidized coenzyme, a POE-POA copolymer and a reagent for measuring a reduced coenzyme
Second Reagent
 A POE-POA alkylaryl ether, surfactant b2, surfactant c, a reagent for measuring a reduced coenzyme, cholesterol ester hydrolase and cholesterol dehydrogenase Kit 89
First Reagent
 A polyanion, an oxidized coenzyme, a POE-POA copolymer, a reagent for measuring a reduced coenzyme, and cholesterol ester hydrolase
Second Reagent
 A POE-POA alkylaryl ether, surfactant b2, surfactant c, a reagent for measuring a reduced coenzyme, and cholesterol dehydrogenase Kit 90
First Reagent
 A polyanion, an oxidized coenzyme, a POE-POA copolymer, a reagent for measuring a reduced coenzyme, and cholesterol ester hydrolase
Second Reagent
 A POE-POA alkylaryl ether, surfactant b2, surfactant c, a reagent for measuring a reduced coenzyme, cholesterol ester hydrolase and cholesterol dehydrogenase Kit 91
First Reagent
 A polyanion, an oxidized coenzyme and surfactant b
Second Reagent
 A POE-POA alkylaryl ether, surfactant c, cholesterol ester hydrolase and cholesterol dehydrogenase Kit 92
First Reagent
 A polyanion, an oxidized coenzyme, surfactant b and cholesterol ester hydrolase
Second Reagent
 A POE-POA alkylaryl ether, surfactant c and cholesterol dehydrogenase Kit 93
First Reagent
 A polyanion, an oxidized coenzyme, surfactant b and cholesterol ester hydrolase
Second Reagent
 A POE-POA alkylaryl ether, surfactant c, cholesterol ester hydrolase and cholesterol dehydrogenase Kit 94
First Reagent
 A polyanion, an oxidized coenzyme, surfactant b and a reagent for measuring a reduced coenzyme
Second Reagent
 A POE-POA alkylaryl ether, surfactant c, a reagent for measuring a reduced coenzyme, cholesterol ester hydrolase and cholesterol dehydrogenase Kit 95
First Reagent
 A polyanion, an oxidized coenzyme, surfactant b, a reagent for measuring a reduced coenzyme, and cholesterol ester hydrolase
Second Reagent
 A POE-POA alkylaryl ether, surfactant c, a reagent for measuring a reduced coenzyme, and cholesterol dehydrogenase Kit 96
First Reagent
 A polyanion, an oxidized coenzyme, surfactant b, a reagent for measuring a reduced coenzyme, and cholesterol ester hydrolase
Second Reagent
 A POE-POA alkylaryl ether, surfactant c, a reagent for measuring a reduced coenzyme, cholesterol ester hydrolase and cholesterol dehydrogenase Kit 97
First Reagent
  A polyanion, an oxidized coenzyme and surfactant b2
Second Reagent
  A POE-POA alkylaryl ether, a POE-POA copolymer, surfactant c, cholesterol ester hydrolase and cholesterol dehydrogenase
Kit 98
First Reagent
  A polyanion, an oxidized coenzyme, surfactant b2 and cholesterol ester hydrolase
Second Reagent
  A POE-POA alkylaryl ether, a POE-POA copolymer, surfactant c and cholesterol dehydrogenase
Kit 99
First Reagent
  A polyanion, an oxidized coenzyme, surfactant b2 and cholesterol ester hydrolase
Second Reagent
  A POE-POA alkylaryl ether, a POE-POA copolymer, surfactant c, cholesterol ester hydrolase and cholesterol dehydrogenase
Kit 100
First Reagent
  A polyanion, an oxidized coenzyme, surfactant b2 and a reagent for measuring a reduced coenzyme
Second Reagent
  A POE-POA alkylaryl ether, a POE-POA copolymer, surfactant c, a reagent for measuring a reduced coenzyme, cholesterol ester hydrolase and cholesterol dehydrogenase
Kit 101
First Reagent
  A polyanion, an oxidized coenzyme, surfactant b2, a reagent for measuring a reduced coenzyme, and cholesterol ester hydrolase
Second Reagent
  A POE-POA alkylaryl ether, a POE-POA copolymer, surfactant c, a reagent for measuring a reduced coenzyme, and cholesterol dehydrogenase
Kit 102
First Reagent
  A polyanion, an oxidized coenzyme, surfactant b2, a reagent for measuring a reduced coenzyme, and cholesterol ester hydrolase
Second Reagent
  A POE-POA alkylaryl ether, a POE-POA copolymer, surfactant c, a reagent for measuring a reduced coenzyme, cholesterol ester hydrolase and cholesterol dehydrogenase
Kit 103
First Reagent
  A polyanion, an oxidized coenzyme and surfactant b
Second Reagent
  A POE-POA alkylaryl ether, surfactant b, surfactant c, cholesterol ester hydrolase and cholesterol dehydrogenase
Kit 104
First Reagent
  A polyanion, an oxidized coenzyme, surfactant b and cholesterol ester hydrolase
Second Reagent
  A POE-POA alkylaryl ether, surfactant b, surfactant c and cholesterol dehydrogenase Kit 105
First Reagent
  A polyanion, an oxidized coenzyme, surfactant b and cholesterol ester hydrolase
Second Reagent
  A POE-POA alkylaryl ether, surfactant b, surfactant c, cholesterol ester hydrolase and cholesterol dehydrogenase
Kit 106
First Reagent
  A polyanion, an oxidized coenzyme, surfactant b and a reagent for measuring a reduced coenzyme
Second Reagent
  A POE-POA alkylaryl ether, surfactant b, surfactant c, a reagent for measuring a reduced coenzyme, cholesterol ester hydrolase and cholesterol dehydrogenase
Kit 107
First Reagent
  A polyanion, an oxidized coenzyme, surfactant b, a reagent for measuring a reduced coenzyme, and cholesterol ester hydrolase
Second Reagent
  A POE-POA alkylaryl ether, surfactant b, surfactant c, a reagent for measuring a reduced coenzyme, and cholesterol dehydrogenase
Kit 108
First Reagent
  A polyanion, an oxidized coenzyme, surfactant b, a reagent for measuring a reduced coenzyme, and cholesterol ester hydrolase
Second Reagent
  A POE-POA alkylaryl ether, surfactant b, surfactant c, a reagent for measuring a reduced coenzyme, cholesterol ester hydrolase and cholesterol dehydrogenase Hereinafter, the present invention will be described more in detail in the following examples. However, these examples are not intended to limit the scope of the present invention. It is to be noted that the reagents, enzymes and surfactants used in the present examples and comparative examples were provided from the manufacturers as described below.

Reagents
  MOPS (manufactured by Dojindo Laboratories)
  DOSE (manufactured by Daito Chemix Corporation)
  Sodium sulfate (manufactured by Kanto Chemical Co., Inc.)
  Dextran sulfate sodium (molecular weight: 500,000) (manufactured by Amersham plc)
  Phosphotungstic acid (manufactured by Nacalai Tesque, Inc.)
  4-Aminoantipyrine (manufactured by Salkyo Kasei K.K.)
Enzymes
  Peroxidase (manufactured by Toyobo Co., Ltd.) CHO-CE (cholesterol oxidase; manufactured by KIKKOMAN Corporation)
  LPL-311 (cholesterol ester hydrolase; manufactured by Toyobo Co., Ltd.)
Surfactants
  Nymeen S-220 (polyoxyethylene octadecylamine; manufactured by NOF Corporation)
  Nymeen L-207 (polyoxyethylene dodecylamine; manufactured by NOF Corporation)
  Ethylenediamine EO40PO40 (an ethylenediamine polyoxyethylene polyoxypropylene copolymer; manufactured by NOF Corporation)

POE-POA Alkylaryl Ethers
  Emulgen L40 (manufactured by Kao Corporation)
  Acronecess KP189R (manufactured by NOF Corporation)
  Acronecess KP189R-40 (manufactured by NOF Corporation)
POE-POA Copolymers
  Pluronic L121 (manufactured by Asahi Denka Kogyo K.K.)
  Acronecess B208 (manufactured by NOF Corporation)
POE Alkenyl Ethers
  BLAUNON EN-1540 (manufactured by Aoki Oil Industrial Co., Ltd.)
  BLAUNON EN-1530 (manufactured by Aoki Oil Industrial Co., Ltd.)
  Nonion E-230 (manufactured by NOF Corporation)
POE Branched Alkyl Ethers
  Nonion OD235 (manufactured by NOF Corporation)
POE-POA Branched Alkyl Ethers
  PEN-4620 (manufactured by Nikko Chemicals Co., Ltd.)
  PEN-4630 (manufactured by Nikko Chemicals Co., Ltd.)
Quaternary Ammonium Salts
  n-Octyltrimethylammonium chloride (manufactured by Tokyo Chemical Industry Co., Ltd.)
  Decyltrimethylammonium bromide (manufactured by Tokyo Chemical Industry Co., Ltd.)
  Lauryltrimethylammonium chloride (manufactured by Nacalai Tesque, Inc.)
  Trimethyltetradecylammonium chloride (manufactured by Tokyo Chemical Industry Co., Ltd.)
  Hexadecyltrimethylammonium chloride (manufactured by Nacalai Tesque, Inc.)
  Trimethylstearylammonium chloride (manufactured by Tokyo Chemical Industry Co., Ltd.)
  Benzyldimethyltetradecylammonium chloride hydrate (manufactured by Tokyo Chemical Industry Co., Ltd.)
  Benzylcetyldimethylammonium chloride hydrate (manufactured by Tokyo Chemical Industry Co., Ltd.)
  Benzyldimethylstearylammonium chloride hydrate (manufactured by Tokyo Chemical Industry Co., Ltd.)
  Cation BB (manufactured by NOF Corporation)
  Cation M2-100 (manufactured by NOF Corporation)
  Morimin 10B (manufactured by Morin Chemical Industries Co., Ltd.)
  Morimin 12B (manufactured by Morin Chemical Industries Co., Ltd.)
Tertiary Amines
  Tertiary Amine BB (manufactured by NOF Corporation)
  N,N-dimethyl-n-decylamine (manufactured by Tokyo Chemical Industry Co., Ltd.)
Primary Amines
  Amine BB (manufactured by NOF Corporation)
  Amine PB (manufactured by NOF Corporation)
  Amine MB (manufactured by NOF Corporation)

EXAMPLES

Example 1

Each of the kits for measuring LDL-C (Kits Aa1 to Aa16) comprising the following first reagent and second reagent was prepared.

First Reagent (Reagent A)

| | |
|---|---|
| MOPS (pH 7.2) | 20 mmol/L |
| Dextran sulfate sodium | 0.5 g/L |
| Sodium sulfate | 2 g/L |
| DOSE | 0.3 g/L |
| Peroxidase | 10 kU/L |

Second Reagent (Reagents a1 to a16)

| | |
|---|---|
| MOPS (pH 7.0) | 20 mmol/L |
| 4-Aminoantipyrine | 0.5 g/L |
| Peroxidase | 20 kU/L |
| Emulgen L40 | 7 g/L |
| Pluronic L121 | 3 g/L |
| LPL-311 | 1.5 kU/L |
| CHO-CE | 1.0 kU/L |

Surfactant c [the types (compound names or product names) thereof and the concentrations thereof are shown in Table 1 below]

Comparative Example 1

A kit for measuring LDL-C (Kit Aa0) comprising the following first reagent (reagent A) and second reagent (reagent a0) was prepared.

First Reagent (Reagent A)

| | |
|---|---|
| MOPS (pH 7.2) | 20 mmol/L |
| Dextran sulfate sodium | 0.5 g/L |
| Sodium sulfate | 2 g/L |
| DOSE | 0.3 g/L |
| Peroxidase | 10 kU/L |

Second Reagent (Reagents a0)

| | |
|---|---|
| MOPS (pH 7.0) | 20 mmol/L |
| 4-Aminoantipyrine | 0.5 g/L |
| Peroxidase | 20 kU/L |
| Emulgen L40 | 7 g/L |
| Pluronic L121 | 3 g/L |
| LPL-311 | 1.5 kU/L |
| CHO-CE | 1.0 kU/L |

Example 2

Using the kits of Example 1 and Comparative Example 1, LDL-C contained in each of 30 human serum samples was measured by the following procedures.

(1) Preparation of Calibration Curve

A normal saline (LDL-C concentration: 0.0 mg/dL) and serum (LDL-C concentration: 140 mg/dL), used as a standard solution, were subjected to measurements using each kit of Example 1 and Comparative Example 1 on Hitachi Auto Analyzer 7170S to give a calibration curve indicating the relationship between the LDL-C concentration and "absorbance".

The term "absorbance" is used herein to mean a value obtained by subtracting E1 from E2, based on two absorbances (E1 and E2) measured by the following reaction.

The standard solution (3 μL) and the first reagent (0.15 mL) were added to a reaction cell, and the obtained solution was then warmed at 37° C. for 5 minutes. The absorbance (E1) of the reaction solution was measured at a main wavelength of 600 nm and at a sub-wavelength of 700 nm. Subsequently, the second reagent (0.05 mL) was added to the reaction solution, and the obtained solution was further warmed at 37° C. for 5 minutes. The absorbance (E2) of the reaction solution was measured at a main wavelength of 600 nm and at a sub-wavelength of 700 nm.

(2) Measurement of "Absorbance" of Human Serum Sample by Reaction of the Sample with Each Kit of Example 1 and Comparative Example 1

The "absorbance" of a human serum sample was measured by the same method as the method of calculating the "absorbance" as described in (1) above, with the exception that the human serum sample was used instead of the standard solution used in the preparation of the calibration curve as described in (1) above.

(3) Determination of LDL-C Concentration in Human Serum Sample

Based on the "absorbance" measured in (2) above and the calibration curve prepared in (1) above, the LDL-C concentration in each of the samples was determined.

Subsequently, using Determiner L LDL-C (manufactured by Kyowa Medex Co., Ltd.) as a commercially available kit for measuring LDL-C, and also using the same 30 human serum samples, LDL-C in each of the samples was measured by the same procedure as described above.

The correlation coefficients obtained between the measurements performed using each of the kits of Example 1 and Comparative Example 1, and the measurements performed using the Determiner L LDL-C kit, are shown in Table 1 below.

Example 3

Whether or not the kit for measuring LDL-C of the present invention can be applied to high TG serum levels was examined. LDL present in a fraction with a gravity of 1.006 to 1.063 was fractionated from normal serum and high TG serum (TG: 1000 mg/dL or more) by an ultracentrifugation method. The fractionated LDL was adjusted to result in cholesterol level of 100 mg/dL. Thereafter, using each of the kits of Example 1 and Comparative Example 1, the LDL-C concentration was measured by the same method as that applied in Example 2. Furthermore, using the following formula (I):

[Expression 1]

$$\text{Measurement value ratio} = \frac{\text{Measurement value } (LDL\text{-}C \text{ in high } TG \text{ serum})}{\text{Measurement value } (LDL\text{-}C \text{ in normal serum})} \quad (I)$$

the measurement value ratio of the LDL-C value in the high TG serum to the LDL-C value in the normal serum was calculated. Herein, as the measurement value ratio is closer to 1, the LDL-C value in the high TG serum can be more precisely measured. The measurement value ratios are shown in Table 1 below.

TABLE 1

| Kit | Surfactant c (second reagent) | Concentration (g/L) | Correlation coefficient | Measurement value ratio |
|---|---|---|---|---|
| Aa0 | — | — | 0.886 | 0.65 |
| Aa1 | n-Octyltrimethylammonium chloride | 5 | 0.964 | 0.74 |
| Aa2 | Decyltrimethyl ammonium bromide | 0.3 | 0.977 | 0.76 |
| Aa3 | Lauryltrimethylammonium chloride | 0.06 | 0.968 | 0.86 |
| Aa4 | Trimethyltetradecylammonium chloride | 0.06 | 0.951 | 0.94 |
| Aa5 | Hexadecyltrimethylammonium chloride | 0.05 | 0.951 | 0.94 |
| Aa6 | Trimethylstearylammonium chloride | 0.05 | 0.943 | 0.94 |
| Aa7 | Morimin 10B (Benzyldimethyldecylammonium chloride) | 0.4 | 0.945 | 0.93 |
| Aa8 | Morimin 12B (Benzyldimethyldodecylammonium chloride) | 0.1 | 0.932 | 0.97 |
| Aa9 | Cation M2-100 (Benzyldimethyltetradecylammonium chloride) | 0.04 | 0.932 | 0.94 |
| Aa10 | Benzylcetyldimethylammonium chloride hydrate | 0.03 | 0.925 | 0.93 |
| Aa11 | Benzyldimethylstearylammonium chloride hydrate | 0.03 | 0.903 | 0.94 |
| Aa12 | Tertiary Amine BB (Dimethyldodecylamine) | 0.04 | 0.942 | 0.89 |
| Aa13 | N,N-dimethyl-n-decylamine | 0.02 | 0.963 | 0.96 |
| Aa14 | Amine BB (Dodecylamine) | 0.05 | 0.951 | 1.02 |
| Aa15 | Amine MB (Tetradecylamine) | 0.05 | 0.952 | 0.80 |
| Aa16 | Amine PB (Cetylamine) | 0.05 | 0.934 | 0.72 |

From the results shown in Table 1, it was found that the measurements performed using the kits containing the quaternary ammonium salt, the tertiary amine or the primary amine (kits Aa1 to Aa16) had a higher correlation with the measurements performed using Determiner L LDL-C, than the measurements performed using a kit (kit Aa0) that did not contain surfactant c (kit Aa0) did.

Moreover, it was also found that the measurements performed using the kits (kits Aa1 to Aa16) containing the quaternary ammonium salt, the tertiary amine or the primary amine had a higher measurement value ratio than the measurement performed using the kit (kit Aa0) that did not contain surfactant c, and further that the measurement value ratio was closer to 1 than the case of the measurement performed using the kit (kit Aa0) that did not contain surfactant c. Accordingly, it was found that, using the kit of the present invention, LDL-C can be precisely measured even in high TG samples.

Comparative Example 2

A kit for measuring LDL-C (kit Ab1) comprising the following first reagent (reagent A) and second reagent (reagents b1 to b3) was prepared.

First Reagent (Reagent A)

| MOPS (pH 7.2) | 20 mmol/L |
| Dextran sulfate sodium | 0.5 g/L |
| Sodium sulfate | 2 g/L |
| DOSE | 0.3 g/L |
| Peroxidase | 10 kU/L |

Second Reagent (Reagents b1 to b3)

| MOPS (pH 7.0) | 20 mmol/L |
| 4-Aminoantipyrine | 0.5 g/L |
| Peroxidase | 20 kU/L |
| Emulgen L40 | 7 g/L |
| Pluronic L121 | 3 g/L |
| LPL-311 | 1.5 kU/L |
| CHO-CE | 1.0 kU/L |

Surfactants (the types and concentrations thereof are shown in Table 2 below)

Comparative Example 3

Using the kits Ab1 to Ab3 of Comparative Example 2, and also using the same 30 human serum samples as those used in Example 2, the correlation coefficients between the measurements performed using the aforementioned kits of Comparative Example 2 and the measurements performed using Determiner L LDL-C were calculated by the same method as that applied in Example 2. The results are shown in Table 2 below.

TABLE 2

| Kit | Surfactant (second reagent) | Concentration (g/L) | Correlation coefficient |
|---|---|---|---|
| Ab1 | Nymeen S-220 | 0.5 | 0.803 |
| Ab2 | Nymeen L-207 | 1.0 | 0.776 |
| Ab3 | Ethylenediamine E040P040 | 0.5 | 0.849 |

From the results shown in Table 2, it was found that the measurements performed using the kits containing the quaternary ammonium salt, the tertiary amine or the primary amine (kits Aa1 to Aa16) had a higher correlation with the measurements performed using Determiner L LDL-C, than the measurements performed using each of the kits of Comparative Example 2 each containing a nitrogen-containing polyoxyethylene surfactant (kits Ab1 to Ab3) did.

Example 4

A kit for measuring LDL-C (kit Ba3) comprising the following first reagent (reagent B) and second reagent (reagents a3) was prepared.

First Reagent (Reagent B)

| MOPS (pH 7.2) | 20 mmol/L |
| Phosphotungstic acid | 0.5 g/L |
| Sodium sulfate | 2 g/L |
| DOSE | 0.3 g/L |
| Peroxidase | 10 kU/L |

Second Reagent (Reagent a3)

| MOPS (pH 7.0) | 20 mmol/L |
| 4-Aminoantipyrine | 0.5 g/L |
| Peroxidase | 20 kU/L |
| Emulgen L40 | 7 g/L |
| Pluronic L121 | 3 g/L |
| LPL-311 | 1.5 kU/L |
| CHO-CE | 1.0 kU/L |
| Lauryltrimethylammonium chloride | 0.06 g/L |

Comparative Example 4

A kit for measuring LDL-C (kit Ca3) comprising the following first reagent (reagent C) and second reagent (reagents a3) was prepared.

First Reagent (Reagent C)

| MOPS (pH 7.2) | 20 mmol/L |
| Sodium sulfate | 2 g/L |
| DOSE | 0.3 g/L |
| Peroxidase | 10 kU/L |

Second Reagent (Reagent a3)

| MOPS (pH 7.0) | 20 mmol/L |
| 4-Aminoantipyrine | 0.5 g/L |
| Peroxidase | 20 kU/L |
| Emulgen L40 | 7 g/L |
| Pluronic L121 | 3 g/L |
| LPL-311 | 1.5 kU/L |
| CHO-CE | 1.0 kU/L |
| Lauryltrimethylammonium chloride | 0.06 g/L |

Example 5

Using the kit Aa3 of Example 1, the kit Ba3 of Example 4 and the kit Ca3 of Comparative Example 4, and also using the same 30 human serum samples as those used in Example 2, the correlation coefficients between the measurements performed using the aforementioned kits and the measurements performed using Determiner L LDL-C were calculated by the same method as that applied in Example 2. The results are shown in Table 3 below.

TABLE 3

| Kit | Polyanion (first reagent) | Concentration (g/L) | Correlation coefficient |
|---|---|---|---|
| Ca3 | — | — | 0.755 |
| Aa3 | Dextran sulfate sodium | 0.5 | 0.968 |
| Ba3 | Phosphotungstic acid | 0.5 | 0.947 |

From the results shown in Table 3, it was found that the measurements performed using the kits containing polyanion (kits Aa3 and Ba3) had a higher correlation with the measurements performed using Determiner L LDL-C, than the measurements performed using the kit of Comparative Example 4 (kit Ca3) that did not contain polyanion.

Example 6

Kits for measuring LDL-C (kits Ac1, Ad1, Ad2, Ae1 and Ae2) comprising the following first reagent (reagent A) and second reagent (reagents c1, d1, d2, e1 and e2) were prepared.

First Reagent (Reagent A)

| | |
|---|---|
| MOPS (pH 7.2) | 20 mmol/L |
| Dextran sulfate sodium | 0.5 g/L |
| Sodium sulfate | 2 g/L |
| DOSE | 0.3 g/L |
| Peroxidase | 10 kU/L |

Second Reagent (Reagents c1, d1, d2, e1 and e2)

| | |
|---|---|
| MOPS (pH 7.0) | 20 mmol/L |
| 4-Aminoantipyrine | 0.5 g/L |
| Peroxidase | 20 kU/L |
| LPL-311 | 1.5 kU/L |
| CHO-CE | 1.0 kU/L |

Surfactants (the types and concentrations thereof are shown in Table 4 below)

Comparative Example 5

Kits for measuring LDL-C (kits Af1, Af2, Ag1 and Ag2) comprising the following first reagent (reagent A) and second reagent (reagents f1, f2, g1 and g2) were prepared.

First Reagent (Reagent A)

| | |
|---|---|
| MOPS (pH 7.2) | 20 mmol/L |
| Dextran sulfate sodium | 0.5 g/L |
| Sodium sulfate | 2 g/L |
| DOSE | 0.3 g/L |
| Peroxidase | 10 kU/L |

Second Reagent (Reagents f1, f2, g1 and g2)

| | |
|---|---|
| MOPS (pH 7.0) | 20 mmol/L |
| 4-Aminoantipyrine | 0.5 g/L |
| Peroxidase | 20 kU/L |
| LPL-311 | 1.5 kU/L |
| CHO-CE | 1.0 kU/L |

Surfactants (the types and concentrations thereof are shown in Table 4 below)

Example 7

Using the kits of Example 6 (kits Ac1, Ad1, Ad2, Ae1 and Ae2) and the kits of Comparative Example 5 (kits Af1, Af2, Ag1 and Ag2), and also using the same 30 human serum samples as those used in Example 2, the correlation coefficients between the measurements performed using the aforementioned kits and the measurements performed using Determiner L LDL-C were calculated by the same method as that applied in Example 2. The results are shown in Table 4 below.

TABLE 4

| | Surfactant (second reagent) | | | | |
|---|---|---|---|---|---|
| Kit | POE-POA alkylaryl ether Acronecess KP189R-40 | POE-POA copolymer Pluronic L121 | POE alkenyl ether BLAUNON EN-1540 | Quaternary ammonium salt | Correlation coefficient |
| Ac1 | 5 g/L | — | 3 g/L | Trimethylstearyl ammonium chloride | 0.953 |
| Ad1 | 5 g/L | 2 g/L | — | | 0.923 |
| Ae1 | 5 g/L | 2 g/L | 3 g/L | | 0.973 |
| Af1 | 5 g/L | — | — | 0.06 g/L | 0.614 |
| Ag1 | — | — | 3 g/L | | −0.523 |
| Ad2 | 5 g/L | 2 g/L | — | Morimin 10B | 0.950 |
| Ae2 | 5 g/L | 2 g/L | 1 g/L | 0.2 g/L | 0.950 |
| Af2 | 5 g/L | — | — | | 0.712 |
| Ag2 | — | — | 1 g/L | | −0.583 |

From the results shown in Table 4, it was found that the measurements performed using the kits of Example 6 (kits Ac1, Ad1, Ad2, Ae1 and Ae2) had a higher correlation with the measurements performed using Determiner L LDL-C, than the measurements performed using the kits of Comparative Example 5 that did not contain surfactant b (kits Af1 and Aft) and using the kits of Comparative Example 5 (kits Ag1 and Ag2) that did not contain a POE-POA alkylaryl ether.

Example 8

A kit for measuring LDL-C (kit Dh1) comprising the following first reagent (reagent D) and second reagent (reagent h1) was prepared.

First Reagent (Reagent D)

| | |
|---|---|
| MOPS (pH 7.2) | 20 mmol/L |
| Dextran sulfate sodium | 1.0 g/L |
| Sodium sulfate | 2 g/L |
| DOSE | 0.3 g/L |
| PEN-4620 | 0.3 g/L |
| Peroxidase | 10 kU/L |

Second Reagent (Reagent h1)

| | |
|---|---|
| MOPS (pH 7.0) | 20 mmol/L |
| 4-Aminoantipyrine | 0.5 g/L |
| Acronecess KP189R-40 | 8 g/L |
| Pluronic L121 | 3 g/L |
| Cation BB | 0.3 g/L |
| Peroxidase | 20 kU/L |
| LPL-311 | 1.0 kU/L |
| CHO-CE | 1.0 kU/L |

Example 9

A kit for measuring LDL-C (kit Eh1) comprising the following first reagent (reagent E) and second reagent (reagent h1) was prepared.
First Reagent (Reagent E)

| | |
|---|---|
| MOPS (pH 7.2) | 20 mmol/L |
| Dextran sulfate sodium | 1.0 g/L |
| Sodium sulfate | 2 g/L |
| DOSE | 0.3 g/L |
| PEN-4630 | 0.3 g/L |
| Peroxidase | 10 kU/L |

Second Reagent (Reagent h1)

| | |
|---|---|
| MOPS (pH 7.0) | 20 mmol/L |
| 4-Aminoantipyrine | 0.5 g/L |
| Acronecess KP189R-40 | 8 g/L |
| Pluronic L121 | 3 g/L |
| Cation BB | 0.3 g/L |
| Peroxidase | 20 kU/L |
| LPL-311 | 1.0 kU/L |
| CHO-CE | 1.0 kU/L |

Example 10

A kit for measuring LDL-C (kit Fi1) comprising the following first reagent (reagent F) and second reagent (reagent i1) was prepared.
First Reagent (Reagent F)

| | |
|---|---|
| MOPS (pH 7.2) | 20 mmol/L |
| Dextran sulfate sodium | 1.0 g/L |
| Sodium sulfate | 2 g/L |
| DOSE | 0.3 g/L |
| BLAUNON EN-1530 | 0.3 g/L |
| Peroxidase | 10 kU/L |

Second Reagent (Reagent i1)

| | |
|---|---|
| MOPS (pH 7.0) | 20 mmol/L |
| 4-Aminoantipyrine | 0.5 g/L |
| Peroxidase | 20 kU/L |
| Acronecess KP189R-40 | 5 g/L |
| Pluronic L121 | 5 g/L |
| Cation BB | 0.3 g/L |
| LPL-311 | 1.5 kU/L |
| CHO-CE | 1.0 kU/L |

Example 11

A kit for measuring LDL-C (kit Fj1) comprising the following first reagent (reagent F) and second reagent (reagent j1) was prepared.
First Reagent (Reagent F)

| | |
|---|---|
| MOPS (pH 7.2) | 20 mmol/L |
| Dextran sulfate sodium | 1.0 g/L |
| Sodium sulfate | 2 g/L |
| DOSE | 0.3 g/L |
| BLAUNON EN-1530 | 0.3 g/L |
| Peroxidase | 10 kU/L |

Second Reagent (Reagent j1)

| | |
|---|---|
| MOPS (pH 7.0) | 20 mmol/L |
| 4-Aminoantipyrine | 0.5 g/L |
| Peroxidase | 20 kU/L |
| Acronecess KP189R | 9 g/L |
| Pluronic L121 | 5 g/L |
| Cation BB | 0.3 g/L |
| LPL-311 | 1.5 kU/L |
| CHO-CE | 1.0 kU/L |

Example 12

A kit for measuring LDL-C (kit Gi1) comprising the following first reagent (reagent G) and second reagent (reagent i1) was prepared.
First Reagent (Reagent G)

| | |
|---|---|
| MOPS (pH 7.2) | 20 mmol/L |
| Dextran sulfate sodium | 1.0 g/L |
| Sodium sulfate | 2 g/L |
| DOSE | 0.3 g/L |
| Nonion E-230 | 0.3 g/L |
| Peroxidase | 10 kU/L |

Second Reagent (Reagent i1)

| | |
|---|---|
| MOPS (pH 7.0) | 20 mmol/L |
| 4-Aminoantipyrine | 0.5 g/L |
| Peroxidase | 20 kU/L |
| Acronecess KP189R-40 | 5 g/L |
| Pluronic L121 | 5 g/L |
| Cation BB | 0.3 g/L |
| LPL-311 | 1.5 kU/L |
| CHO-CE | 1.0 kU/L |

Example 13

A kit for measuring LDL-C (kit Gj1) comprising the following first reagent (reagent G) and second reagent (reagent j1) was prepared.

First Reagent (Reagent G)

| | |
|---|---|
| MOPS (pH 7.2) | 20 mmol/L |
| Dextran sulfate sodium | 1.0 g/L |
| Sodium sulfate | 2 g/L |
| DOSE | 0.3 g/L |
| Nonion E-230 | 0.3 g/L |
| Peroxidase | 10 kU/L |

Second Reagent (Reagent j1)

| | |
|---|---|
| MOPS (pH 7.0) | 20 mmol/L |
| 4-Aminoantipyrine | 0.5 g/L |
| Peroxidase | 20 kU/L |
| Acronecess KP189R | 9 g/L |
| Pluronic L121 | 5 g/L |
| Cation BB | 0.3 g/L |
| LPL-311 | 1.5 kU/L |
| CHO-CE | 1.0 kU/L |

Example 14

A kit for measuring LDL-C (kit Hi1) comprising the following first reagent (reagent H) and second reagent (reagent i1) was prepared.

First Reagent (Reagent H)

| | |
|---|---|
| MOPS (pH 7.2) | 20 mmol/L |
| Dextran sulfate sodium | 1.0 g/L |
| Sodium sulfate | 2 g/L |
| DOSE | 0.3 g/L |
| Nonion OD230 | 0.3 g/L |
| Peroxidase | 10 kU/L |

Second Reagent (Reagent i1)

| | |
|---|---|
| MOPS (pH 7.0) | 20 mmol/L |
| 4-Aminoantipyrine | 0.5 g/L |
| Peroxidase | 20 kU/L |
| Acronecess KP189R-40 | 5 g/L |
| Pluronic L121 | 5 g/L |
| Cation BB | 0.3 g/L |
| LPL-311 | 1.5 kU/L |
| CHO-CE | 1.0 kU/L |

Example 15

A kit for measuring LDL-C (kit Hj1) comprising the following first reagent (reagent H) and second reagent (reagent j1) was prepared.

First Reagent (Reagent H)

| | |
|---|---|
| MOPS (pH 7.2) | 20 mmol/L |
| Dextran sulfate sodium | 1.0 g/L |
| Sodium sulfate | 2 g/L |
| DOSE | 0.3 g/L |
| Nonion OD230 | 0.3 g/L |
| Peroxidase | 10 kU/L |

Second Reagent (Reagent j1)

| | |
|---|---|
| MOPS (pH 7.0) | 20 mmol/L |
| 4-Aminoantipyrine | 0.5 g/L |
| Peroxidase | 20 kU/L |
| Acronecess KP189R | 9 g/L |
| Pluronic L121 | 5 g/L |
| Cation BB | 0.3 g/L |
| LPL-311 | 1.5 kU/L |
| CHO-CE | 1.0 kU/L |

Example 16

A kit for measuring LDL-C (kit Hk1) comprising the following first reagent (reagent H) and second reagent (reagent k1) was prepared.

First Reagent (Reagent H)

| | |
|---|---|
| MOPS (pH 7.2) | 20 mmol/L |
| Dextran sulfate sodium | 1.0 g/L |
| Sodium sulfate | 2 g/L |
| DOSE | 0.3 g/L |
| Nonion OD230 | 0.3 g/L |
| Peroxidase | 10 kU/L |

Second Reagent (Reagent k1)

| | |
|---|---|
| MOPS (pH 7.0) | 20 mmol/L |
| 4-Aminoantipyrine | 0.5 g/L |
| Peroxidase | 20 kU/L |
| Acronecess KP189R | 9 g/L |
| Pluronic L121 | 5 g/L |
| Trimethyldecylammonium chloride | 0.5 g/L |
| LPL-311 | 1.5 kU/L |
| CHO-CE | 1.0 kU/L |

Example 17

A kit for measuring LDL-C (kit Il1) comprising the following first reagent (reagent I) and second reagent (reagent l1) was prepared.

First Reagent (Reagent I)

| | |
|---|---|
| MOPS (pH 7.2) | 20 mmol/L |
| Dextran sulfate sodium | 1.0 g/L |
| Sodium sulfate | 2 g/L |
| DOSE | 0.3 g/L |
| Acronecess B208 | 1.3 g/L |
| LPL311 | 0.4 kU/L |
| Peroxidase | 10 kU/L |

Second Reagent (Reagent l1)

| MOPS (pH 7.0) | 20 mmol/L |
|---|---|
| 4-Aminoantipyrine | 0.5 g/L |
| Acronecess KP189R-40 | 5 g/L |
| Cation BB | 0.1 g/L |
| CHO-CE | 1.0 kU/L |
| Peroxidase | 20 kU/L |

Example 18

A kit for measuring LDL-C (kit Jm1) comprising the following first reagent (reagent J) and second reagent (reagent m1) was prepared.

First Reagent (Reagent J)

| MOPS (pH 7.2) | 20 mmol/L |
|---|---|
| Dextran sulfate sodium | 1.0 g/L |
| Sodium sulfate | 2 g/L |
| DOSE | 0.3 g/L |
| Acronecess B208 | 1 g/L |
| Peroxidase | 10 kU/L |

Second Reagent (Reagent m1)

| MOPS (pH 7.0) | 20 mmol/L |
|---|---|
| 4-Aminoantipyrine | 0.5 g/L |
| Acronecess KP189R-40 | 7 g/L |
| Pluronic L121 | 3 g/L |
| Cation BB | 0.2 g/L |
| CHO-CE | 1.0 kU/L |
| LPL311 | 1.2 kU/L |
| Peroxidase | 20 kU/L |

Example 19

Using the kits of Examples 8 to 18, and also using the same 30 human serum samples as those used in Example 2, the measurement was carried out by the same method as that applied in Example 2, so as to determine the concentration of LDL-C in each of the samples. Similarly, the same samples as those used above were subjected to the measurement using Determiner L LDL-C, so as to determine the concentration of LDL-C in each sample. Subsequently, the correlation coefficients between the measurements performed using the aforementioned kits of Examples 8 to 18 and the measurements performed using Determiner L LDL-C were calculated. The results are shown in Table 5 below.

TABLE 5

| Kit | Correlation coefficient |
|---|---|
| Dh1 | 0.991 |
| Eh1 | 0.992 |
| Fi1 | 0.987 |
| Fj1 | 0.997 |
| Gi1 | 0.987 |
| Gj1 | 0.997 |
| Hi1 | 0.988 |

TABLE 5-continued

| Kit | Correlation coefficient |
|---|---|
| Hj1 | 0.997 |
| Hk1 | 0.994 |
| Il1 | 0.982 |
| Jm1 | 0.987 |

From the results shown in Table 5, it was found that the measurements performed using the kits comprising the first reagent comprising a POE-POA copolymer, a POE alkenyl ether, a POE branched alkyl ether or a POE-POA branched alkyl ether, had also an extremely good correlation with the measurements performed using Determiner L LDL-C.

Example 20

Kits for measuring LDL-C (kits Kn1 to Kn4) comprising the following first reagent (reagent K) and second reagent (reagents n1 to n4) were prepared.

First Reagent (Reagent K)

| MOPS (pH 7.2) | 20 mmol/L |
|---|---|
| Dextran sulfate sodium | 1.0 g/L |
| Sodium sulfate | 2 g/L |
| DOSE | 0.3 g/L |
| Acronecess B208 | 1 g/L |
| Peroxidase | 10 kU/L |
| LPL311 | 0.4 kU/L |

Second Reagent (Reagents n1 to n4)

| MOPS (pH 7.0) | 20 mmol/L |
|---|---|
| 4-Aminoantipyrine | 0.5 g/L |
| Acronecess KP189R-40 | 7 g/L |
| Pluronic L121 | 3 g/L |
| Peroxidase | 20 kU/L |
| CHO-CE | 1.0 kU/L |

Surfactant c (the types and concentrations thereof are shown in Table 6 below)

Example 21

Kits for measuring LDL-C (kits Lo1 to Lo5) comprising the following first reagent (reagent L) and second reagent (reagents o1 to o5) were prepared.

First Reagent (Reagent L)

| MOPS (pH 6.5) | 20 mmol/L |
|---|---|
| Dextran sulfate sodium | 0.75 g/L |
| Sodium sulfate | 2 g/L |
| DOSE | 0.3 g/L |
| Peroxidase | 10 kU/L |

Second Reagent (Reagents o1 to o5)

| MOPS (pH 7.0) | 20 mmol/L |
|---|---|
| 4-Aminoantipyrine | 0.5 g/L |
| Peroxidase | 20 kU/L |
| Acronecess KP189R | 13 g/L |

-continued

| | |
|---|---|
| Pluronic L121 | 7 g/L |
| LPL-311 | 1.5 kU/L |
| CHO-CE | 2.0 kU/L |

Surfactant c (the types and concentrations thereof are shown in Table 6 below)

Example 22

Using the kits of Examples 20 and 21, and also using the same 30 human serum samples as those used in Example 2, the measurement was carried out by the same method as that applied in Example 2, so as to determine the concentration of LDL-C in each of the samples. Similarly, the same samples as those used above were subjected to the measurement using Determiner L LDL-C, so as to determine the concentration of LDL-C in each of the samples. Subsequently, the correlation coefficients between the measurements performed using the aforementioned kits of Examples 20 and 21 and the measurements performed using Determiner L LDL-C were calculated. The results are shown in Table 6 below.

TABLE 6

| | Second reagent | | |
|---|---|---|---|
| Kit | Surfactant c | Concentration (g/L) | Correlation coefficient |
| Kn1 | Cation BB | 0.2 | 0.989 |
| Kn2 | Morimin 10B | 0.2 | 0.995 |
| Kn3 | Morimin 12B | 0.05 | 0.986 |
| Kn4 | Tertiary amine BB | 0.06 | 0.978 |
| Lo1 | Decyltrimethylammonium bromide | 0.5 | 0.996 |
| Lo2 | Lauryltrimethylammonium chloride | 0.08 | 0.997 |
| Lo3 | Trimethyltetradecylammonium chloride | 0.05 | 0.995 |
| Lo4 | Morimin 10B | 0.2 | 0.998 |
| Lo5 | Morimin 12B | 0.04 | 0.993 |

From the results shown in Table 6, it was found that the measurements performed using the kits containing a POE-POA alkylaryl ether, a POE-POA copolymer and surfactant c had also an extremely good correlation with the measurements performed using Determiner L LDL-C.

Example 23

Kits for measuring LDL-C (kits Mp1, Aq1 and Mr1) comprising the following first reagent and second reagent were prepared.

First Reagent (Reagent M or Reagent A)

| | |
|---|---|
| MOPS (pH 7.2) | 20 mmol/L |
| Dextran sulfate sodium | 0.5 g/L |
| Sodium sulfate | 2 g/L |
| DOSE | 0.3 g/L |

Surfactant b2 (the types and concentrations are shown in Table 7 below)

| | |
|---|---|
| Peroxidase | 10 kU/L |

Second Reagent (Reagents p1, q1 and r1)

| | |
|---|---|
| MOPS (pH 7.0) | 20 mmol/L |
| 4-Aminoantipyrine | 0.5 g/L |
| Peroxidase | 20 kU/L |

POE-POA alkylaryl ether (the types and concentrations are shown in Table 7 below)

Surfactant b1 (the types and concentrations are shown in Table 7 below)

Surfactant b2 (the types and concentrations are shown in Table 7 below)

Surfactant c (the types and concentrations are shown in Table 7 below)

| | |
|---|---|
| LPL-311 | 1.5 kU/L |
| CHO-CE | 1.0 kU/L |

Comparative Example 6

Kits for measuring LDL-C (kits Mp0, Aq0 and Mr0) comprising the following first reagent and second reagent were prepared.

First Reagent (Reagent M or Reagent A)

| | |
|---|---|
| MOPS (pH 7.2) | 20 mmol/L |
| Dextran sulfate sodium | 0.5 g/L |
| Sodium sulfate | 2 g/L |
| DOSE | 0.3 g/L |

Surfactant b2 (the types and concentrations are shown in Table 7 below)

| | |
|---|---|
| Peroxidase | 10 kU/L |

Second Reagent (Reagents p0, q0 and r0)

| | |
|---|---|
| MOPS (pH 7.0) | 20 mmol/L |
| 4-Aminoantipyrine | 0.5 g/L |
| Peroxidase | 20 kU/L |

POE-POA alkylaryl ether (the types and concentrations are shown in Table 7 below)

Surfactant b1 (the types and concentrations are shown in Table 7 below)

Surfactant b2 (the types and concentrations are shown in Table 7 below)

| | |
|---|---|
| LPL-311 | 1.5 kU/L |
| CHO-CE | 1.0 kU/L |

Example 24

Using the kits of Examples 23 (kits Mp1, Aq1 and Mr1) and the kits of Comparative Example 6 (kits Mp0, Aq0 and Mr0), and also using 30 human serum samples (which were different from those used in Example 2), the correlation coefficients between the measurements performed using the aforementioned kits and the measurements performed using Determiner L LDL-C were calculated by the same method as that applied in Example 2. The results are shown in Table 7 below.

TABLE 7

| | | Surfactant | | | | |
|---|---|---|---|---|---|---|
| | First reagent | Second reagent | | | | |
| Kit | Surfactant b2 | POE-POA alkylaryl ether | Surfactant b1 | Surfactant b2 | Surfactant c | Correlation coefficient |
| Mp1 | Nonion E-230 (0.3 g/L) | Acronecess KP189R (13 g/L) | Pluronic L121 (7 g/L) | — | Lauryltrimethylammonium chloride (0.1 g/L) | 0.976 |
| Mp0 | Nonion E-230 (0.3 g/L) | Acronecess KP189R (13 g/L) | Pluronic L121 (7 g/L) | — | — | 0.827 |
| Aq1 | — | Acronecess KP189R-40 (2 g/L) | Pluronic L121 (5 g/L) | BLAUNON EN-1540 (3 g/L) | Trimethylstearylammonium chloride (0.06 g/L) | 0.899 |
| Aq0 | — | Acronecess KP189R-40 (2 g/L) | Pluronic L121 (5 g/L) | BLAUNON EN-1540 (3 g/L) | — | 0.631 |
| Mr1 | Nonion E-230 (0.3 g/L) | Acronecess KP189R-40 (5 g/L) | Pluronic L121 (5 g/L) | — | Cation BB (0.3 g/L) | 0.952 |
| Mr0 | Nonion E-230 (0.3 g/L) | Acronecess KP189R-40 (5 g/L) | Pluronic L121 (5 g/L) | — | — | 0.671 |

From the results shown in Table 7, it was found that the measurements performed using the kits of Example 23 (kit Mp1, Aq1 and Mr1) had a higher correlation with the measurements performed using Determiner L LDL-C, than the measurements performed using the kits of Comparative Examples 6 that did not contain surfactant c (kits Mp0, Aq0 and Mr0).

INDUSTRIAL APPLICABILITY

According to the present invention, there are provided a method, a reagent, and a kit for measuring LDL-C, which are useful for the diagnosis of metabolic syndrome, arteriosclerosis, and the like.

The invention claimed is:

1. A method for measuring cholesterol in low-density lipoprotein contained in a sample, which comprises the steps of:
reacting the sample with (i) a combination of cholesterol ester hydrolase and cholesterol oxidase or (ii) a combination of cholesterol ester hydrolase, an oxidized coenzyme and cholesterol dehydrogenase in the presence of:

[a] a polyoxyethylene-polyoxyalkylene alkylaryl ether;

[b] one or more surfactants selected from the group consisting of a polyoxyethylene-polyoxyalkylene copolymer, a polyoxyethylene alkenyl ether, a polyoxyethylene branched alkyl ether, and a polyoxyethylene-polyoxyalkylene branched alkyl ether;

[c] one or more surfactants selected from the group consisting of a primary amine, a secondary amine, a tertiary amine, and a quaternary ammonium, wherein the tertiary amine is a dimethylalkylamine; and

[d] a polyanion, and measuring for (i), an amount of hydrogen peroxide formed or oxygen consumed; or for (ii), an amount of reduced coenzyme formed or oxidized coenzyme consumed.

2. The method according to claim 1, wherein said surfactant [b] is a polyoxyethylene-polyoxyalkylene copolymer.

3. The method according to claim 1, wherein the formed substance is hydrogen peroxide.

4. The method according to claim 3, wherein the hydrogen peroxide is measured using a reagent for measuring hydrogen peroxide.

5. The method according to claim 1, wherein the formed substance is a reduced coenzyme.

6. The method according to claim 5, wherein the reduced coenzyme is measured using a reagent for measuring a reduced coenzyme.

7. A method for measuring cholesterol in low-density lipoprotein contained in a sample, which comprises the steps of:
reacting the sample with (i) a combination of cholesterol ester hydrolase and cholesterol oxidase or (ii) a combination of cholesterol ester hydrolase, an oxidized coenzyme and cholesterol dehydrogenase in the presence of:

[a] a polyoxyethylene-polyoxyalkylene alkylaryl ether;

[b] a polyoxyethylene-polyoxyalkylene copolymer; and one or more surfactants selected from the group consisting of a polyoxyethylene alkenyl ether, a polyoxyethylene branched alkyl ether, and a polyoxyethylene-polyoxyalkylene branched alkyl ether;

[c] one or more surfactants selected from the group consisting of a primary amine, a secondary amine, a tertiary amine, and a quaternary ammonium, wherein the tertiary amine is a dimethylalkylamine; and

[d] a polyanion, and measuring for (i), an amount of hydrogen peroxide formed or oxygen consumed; or for (ii), an amount of reduced coenzyme formed or oxidized coenzyme consumed.

8. A method for measuring cholesterol in low-density lipoprotein contained in a sample, which comprises the steps of:
reacting the sample with (i) a combination of cholesterol ester hydrolase and cholesterol oxidase or (ii) a combination of cholesterol ester hydrolase, an oxidized coenzyme and cholesterol dehydrogenase in the presence of:

[a] a polyoxyethylene-polyoxyalkylene alkylaryl ether;

[b] one or more surfactants selected from the group consisting of a polyoxyethylene-polyoxyalkylene, a polyoxyethylene alkenyl ether, a polyoxyethylene branched alkyl ether, and a polyoxyethylene-polyoxyalkylene branched alkyl ether;

[c] a surfactant selected from a trimethylalkylammonium salt or a benzyldimethylalklyammonium salt;

[d] a polyanion;

measuring for (i), an amount of hydrogen peroxide formed or oxygen consumed; or for (ii), an amount of reduced coenzyme formed or oxidized coenzyme consumed.

9. A method for measuring cholesterol in low-density lipoprotein contained in a sample, which comprises the steps of:
reacting the sample with (i) a combination of cholesterol ester hydrolase and cholesterol oxidase or (ii) a combination of cholesterol ester hydrolase, an oxidized coenzyme and cholesterol dehydrogenase in the presence of:

[a] a polyoxyethylene-polyoxyalkylene alkylaryl ether;

[b] one or more surfactants selected from the group consisting of a polyoxyethlene-polyoxyalkylene, a polyoxyethylene alkenyl ether, a polyoxyethylene branched alkyl ether, and a polyoxyethylene-polyoxyalkylene branched alkyl ether;

[c] a dimethylalkylamine surfactant; and

[d] a polyanion; and measuring for (i), an amount of hydrogen peroxide formed or oxygen consumed; or for (ii), an amount of reduced coenzyme formed or oxidized coenzyme consumed.

10. A reagent for measuring cholesterol in low-density lipoprotein contained in a sample, which comprises:

[a] a polyoxyethylene-polyoxyalkylene alkylaryl ether;

[b] one or more surfactants selected from the group consisting of a polyoxyethylene-polyoxyalkylene copolymer, a polyoxyethylene alkenyl ether, a polyoxyethylene branched alkyl ether, and a polyoxyethylene-polyoxyalkylene branched alkyl ether;

[c] one or more surfactants selected from the group consisting of a primary amine, a secondary amine, a tertiary amine, wherein the tertiary amine is a dimethylalkylamine, and a quaternary ammonium;

[d] a polyanion; and cholesterol ester hydrolase and cholesterol oxidase.

11. The reagent according to claim 10, wherein said surfactant [b] is a polyoxyethylene-polyoxyalkylene copolymer.

12. The reagent according to claim 10, which further comprises a reagent for measuring a substance formed as a result of the reaction of the cholesterol ester hydrolase and the cholesterol oxidase with the sample.

13. The reagent according to claim 12, wherein the substance formed as a result of the reaction of the cholesterol ester hydrolase and the cholesterol oxidase with the sample is hydrogen peroxide.

14. A reagent for measuring cholesterol in low-density lipoprotein contained in a sample, which comprises:

[a] a polyoxyethylene-polyoxyalkylene alkylaryl ether;

[b] a polyoxyethylene-polyoxyalkylene copolymer; and one or more surfactants selected from the group consisting of a polyoxyethylene alkenyl ether, a polyoxyethylene branched alkyl ether, and a polyoxyethylene-polyoxyalkylene branched alkyl ether;

[c] one or more surfactants selected from the group consisting of a primary amine, a secondary amine, a tertiary amine, wherein the tertiary amine is a dimethylalkylamine, and a quaternary ammonium;

[d] a polyanion, and cholesterol ester hydrolase and cholesterol oxidase.

15. A reagent for measuring cholesterol in low-density lipoprotein contained in a sample, which comprises:

[a] a polyoxyethylene-polyoxyalkylene alkylaryl ether;

[b] one or more surfactants selected from the group consisting of a polyoxyethylene-polyoxyalkylene copolymer, a polyoxyethylene alkenyl ether, a polyoxyethylene branched alkyl ether, and a polyoxyethylene-polyoxyalkylene branched alkyl ether;

[c] one or more surfactants selected from the group consisting of a primary amine, a secondary amine, a tertiary amine, and a quaternary ammonium, wherein the tertiary amine is a dimethylalkylamine;

[d] a polyanion; and cholesterol ester hydrolase, an oxidized coenzyme, and cholesterol dehydrogenase.

16. The reagent according to claim 15, wherein said surfactant [b] is a polyoxyethylene-polyoxyalkylene copolymer.

17. The reagent according to claim 15, which further comprises a reagent for measuring the substance formed as a result of the reaction of the cholesterol ester hydrolase, the oxidized coenzyme, and the cholesterol dehydrogenase with the sample.

18. The reagent according to claim 17, wherein the substance formed as a result of the reaction of the cholesterol ester hydrolase, the oxidized coenzyme, and the cholesterol dehydrogenase with the sample is a reduced coenzyme.

19. A reagent for measuring cholesterol in low-density lipoprotein contained in a sample, which comprises:

[a] a polyoxyethylene-polyoxyalkylene alkylaryl ether;

[b] a polyoxyethylene-polyoxyalkylene copolymer; and one or more surfactants selected from the group consisting of a polyoxyethylene alkenyl ether, a polyoxyethylene branched alkyl ether, and a polyoxyethylene-polyoxyalkylene branched alkyl ether;

[c] one or more surfactants selected from the group consisting of a primary amine, a secondary amine, a tertiary amine, wherein the tertiary amine is a dimethylalkylamine, and a quaternary ammonium;

[d] a polyanion, and cholesterol ester hydrolase, an oxidized coenzyme, and cholesterol dehydrogenase.

20. A reagent for measuring cholesterol in low-density lipoprotein contained in a sample, which comprises:

[a] a polyoxyethylene-polyoxyalkylene alkylaryl ether;

[b] one or more surfactants selected from the group consisting of a polyoxyethylene-polyoxyalkylene copolymer, a polyoxyethylene alkenyl ether, a polyoxyethylene branched alkyl ether, and a polyoxyethylene-polyoxyalkylene branched alkyl ether;
[c] a surfactant selected from a trimethylalkylammonium salt or a benzyldimethylalkylammonium salt;
[d] a polyanion, and
cholesterol ester hydrolase and cholesterol oxidase.

21. A reagent for measuring cholesterol in low-density lipoprotein contained in a sample, which comprises:
[a] a polyoxyethylene-polyoxyalkylene alkylaryl ether;
[b] one or more surfactants selected from the group consisting of a polyoxyethylene-polyoxyalkylene copolymer, a polyoxyethylene alkenyl ether, a polyoxyethylene branched alkyl ether, and a polyoxyethylene-polyoxyalkylene branched alkyl ether;
[c] a dimethylalkylamine surfactant;
[d] a polyanion, and
cholesterol ester hydrolase and cholesterol oxidase.

22. A kit for measuring cholesterol in low-density lipoprotein contained in a sample, which comprises
a first reagent comprising at least one selected from the group consisting of:
[a] a polyoxyethylene-polyoxyalkylene alkylaryl ether;
[b] one or more surfactants selected from the group consisting of a polyoxyethylene-polyoxyalkylene copolymer, a polyoxyethylene alkenyl ether, a polyoxyethylene branched alkyl ether, and a polyoxyethylene-polyoxyalkylene branched alkyl ether;
[c] one or more surfactants selected from the group consisting of a primary amine, a secondary amine, a tertiary amine, and a quaternary ammonium;
[d] a polyanion; and
cholesterol ester hydrolase, and
a second reagent comprising cholesterol oxidase, wherein each of the above described elements [a] to [d] and the cholesterol ester hydrolase is contained in either the first or second reagent, or in both of the first and second reagents.

23. The kit according to claim 22, wherein said surfactant [b] is a polyoxyethylene-polyoxyalkylene copolymer.

24. The kit according to claim 22, wherein said surfactant [b] is
a polyoxyethylene-polyoxyalkylene copolymer; and
one or more surfactants selected from the group consisting of a polyoxyethylene alkenyl ether, a polyoxyethylene branched alkyl ether, and a polyoxyethylene-polyoxyalkylene branched alkyl ether.

25. The kit according to claim 22, which further comprises a reagent for measuring hydrogen peroxide in at least one of the first or second reagents.

26. A kit for measuring cholesterol in low-density lipoprotein contained in a sample, which comprises
a first reagent comprising at least one selected from the group consisting of:
[a] a polyoxyethylene-polyoxyalkylene alkylaryl ether;
[b] one or more surfactants selected from the group consisting of a polyoxyethylene-polyoxyalkylene copolymer, a polyoxyethylene alkenyl ether, a polyoxyethylene branched alkyl ether, and a polyoxyethylene-polyoxyalkylene branched alkyl ether;
[c] one or more surfactants selected from the group consisting of a primary amine, a secondary amine, a tertiary amine, and a quaternary ammonium;
[d] a polyanion;
an oxidized coenzyme; and cholesterol ester hydrolase, and
a second reagent comprising cholesterol dehydrogenase, wherein each of the above described elements [a] to [d], the oxidized coenzyme, and the cholesterol ester hydrolase is contained in either the first or second reagent, or in both of the first and second reagents.

27. The kit according to claim 26, wherein said surfactant [b] is a polyoxyethylene-polyoxyalkylene copolymer.

28. The kit according to claim 26, wherein said surfactant [b] is
a polyoxyethylene-polyoxyalkylene copolymer; and
one or more surfactants selected from the group consisting of a polyoxyethylene alkenyl ether, a polyoxyethylene branched alkyl ether, and a polyoxyethylene-polyoxyalkylene branched alkyl ether.

29. The kit according to claim 26, which further comprises a reagent for measuring a reduced coenzyme in at least one of the first or second reagents.

30. The kit according to claim 22 or 26, wherein the surfactant [c] is a trimethylalkylammonium salt or a benzyldimethylalkylammonium salt.

31. The kit according to claim 22 or 26, wherein the surfactant [c] is a dimethylalkylamine.

32. A reagent for measuring cholesterol in low-density lipoprotein contained in a sample, which comprises:
[a] a polyoxyethylene-polyoxyalkylene alkylaryl ether;
[b] one or more surfactants selected from the group consisting of a polyoxyethylene-polyoxyalkylene copolymer, a polyoxyethylene alkenyl ether, a polyoxyethylene branched alkyl ether, and a polyoxyethylene-polyoxyalkylene branched alkyl ether;
[c] a surfactant selected from a trimethylalkylammonium salt or a benzyldimethylalklyammonium salt;
[d] a polyanion, and
cholesterol ester hydrolase, an oxidized coenzyme, and cholesterol dehydrogenase.

33. A reagent for measuring cholesterol in low-density lipoprotein contained in a sample, which comprises:
[a] a polyoxyethylene-polyoxyalkylene alkylaryl ether;
[b] one or more surfactants selected from the group consisting of a polyoxyethylene-polyoxyalkylene copolymer, a polyoxyethylene alkenyl ether, a polyoxyethylene branched alkyl ether, and a polyoxyethylene-polyoxyalkylene branched alkyl ether;
[c] a dimethylalkylamine surfactant;
[d] a polyanion, and
cholesterol ester hydrolase, an oxidized coenzyme, and cholesterol dehydrogenase.

* * * * *